US011573522B2

(12) United States Patent
Maeta et al.

(10) Patent No.: US 11,573,522 B2
(45) Date of Patent: Feb. 7, 2023

(54) IMAGE FORMING APPARATUS PERMITTING USER TO IMAGINE CLEAR DETACHMENT PROCEDURE OF TONER CARTRIDGE FROM PROCESS CARTRIDGE

(71) Applicant: Brother Kogyo Kabushiki Kaisha, Nagoya (JP)

(72) Inventors: Daisuke Maeta, Nagoya (JP); Shougo Sato, Seto (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 0 days.

(21) Appl. No.: 17/652,944

(22) Filed: Mar. 1, 2022

(65) Prior Publication Data

US 2022/0183636 A1 Jun. 16, 2022

Related U.S. Application Data

(63) Continuation of application No. 17/094,149, filed on Nov. 10, 2020, now Pat. No. 11,366,422.

(30) Foreign Application Priority Data

Nov. 13, 2019 (JP) ............................ JP2019-205799

(51) Int. Cl.
*G03G 21/18* (2006.01)
*G06T 7/70* (2017.01)
(Continued)

(52) U.S. Cl.
CPC ........... *G03G 21/1825* (2013.01); *A61B 5/01* (2013.01); *A61B 5/7246* (2013.01); *A61B 5/742* (2013.01);
(Continued)

(58) Field of Classification Search
CPC ........... G03G 15/0886; G03G 21/1676; G03G 15/0875; G03G 15/0896; G03G 15/0872;
(Continued)

(56) References Cited

U.S. PATENT DOCUMENTS

2010/0166453 A1* 7/2010 Okabe ................ G03G 15/0194 399/119
2010/0166457 A1* 7/2010 Hashimoto ........ G03G 15/0813 399/117

(Continued)

FOREIGN PATENT DOCUMENTS

JP 2017-146512 A 8/2017
JP 2018-066817 A 4/2018

*Primary Examiner* — Jessica L Eley
(74) *Attorney, Agent, or Firm* — Burr Patent Law, PLLC

(57) ABSTRACT

An image forming apparatus includes a housing and a first process cartridge. The first process cartridge is attachable to and detachable from the housing. The first process cartridge includes a first photosensitive drum, a first developing roller, and a developing frame. The developing frame has a toner inlet opening. The toner cartridge has a toner supply opening. The toner cartridge is positioned above the developing frame such that the toner supply opening and the toner inlet opening face with each other in upward/downward direction. In the state where the first process cartridge to which the toner cartridge is attached is attached to the housing, the toner cartridge is incapable of being detached from the first process cartridge. In a state where the first process cartridge to which the toner cartridge is attached is detached from the housing, the toner cartridge is detachable from the first process cartridge.

22 Claims, 26 Drawing Sheets

(51) Int. Cl.

| | |
|---|---|
| ***G07C 9/30*** | (2020.01) |
| ***A61B 5/01*** | (2006.01) |
| ***A61B 5/00*** | (2006.01) |
| ***G01J 5/00*** | (2022.01) |
| ***G01J 5/02*** | (2022.01) |
| ***G01J 5/10*** | (2006.01) |
| ***G08B 21/02*** | (2006.01) |
| ***H04N 5/38*** | (2006.01) |
| ***H04N 5/76*** | (2006.01) |
| ***H04N 7/18*** | (2006.01) |
| ***H04R 1/02*** | (2006.01) |

(52) U.S. Cl.
CPC ............ *A61B 5/7405* (2013.01); *A61B 5/746* (2013.01); *G01J 5/0025* (2013.01); *G01J 5/025* (2013.01); *G01J 5/10* (2013.01); *G03G 21/1846* (2013.01); *G06T 7/70* (2017.01); *G07C 9/30* (2020.01); *G08B 21/02* (2013.01); *H04N 5/38* (2013.01); *H04N 5/76* (2013.01); *H04N 7/18* (2013.01); *H04R 1/028* (2013.01); *G06T 2207/30196* (2013.01); *G06T 2207/30242* (2013.01)

(58) Field of Classification Search
CPC ........... G03G 21/1842; G03G 21/1821; G03G 15/0142; G03G 21/1623
See application file for complete search history.

(56) References Cited

U.S. PATENT DOCUMENTS

| | | | | |
|---|---|---|---|---|
| 2010/0260514 | A1* | 10/2010 | Suzuki | G03G 15/0194 399/111 |
| 2013/0051849 | A1 | 2/2013 | Itabashi et al. | |
| 2017/0153596 | A1 | 6/2017 | Takahashi et al. | |
| 2017/0343914 | A1 | 11/2017 | Suzuki et al. | |
| 2018/0107153 | A1 | 4/2018 | Sato et al. | |
| 2018/0173133 | A1* | 6/2018 | Tsukada | G03G 21/1619 |

* cited by examiner

IMAGE FORMING APPARATUS PERMITTING USER TO IMAGINE CLEAR DETACHMENT PROCEDURE OF TONER CARTRIDGE FROM PROCESS CARTRIDGE

CROSS REFERENCE TO RELATED APPLICATION

This application is a Continuation Application of U.S. patent application Ser. No. 17/094,149 filed Nov. 10, 2020, and claims priority under 35 U.S.C. § 119 from Japanese Patent Application No. 2019-205799 filed Nov. 13, 2019, the entireties of which are incorporated herein by reference.

TECHNICAL FIELD

The present disclosure relates to an image forming apparatus.

BACKGROUND

There has been known an image forming apparatus including a housing, a process cartridge which includes a photosensitive drum and a developing roller, and a toner cartridge accommodating therein toner. The toner cartridge is attachable to and detachable from the process cartridge. The process cartridge to which the toner cartridge is attached is attachable to and detachable from the housing. (See Japanese Patent Application Publication No. 2017-146512).

In such type of image forming apparatus, the process cartridge is attached to the housing with such a posture that the toner cartridge is positioned above the process cartridge. The toner cartridge has a lower end portion formed with a toner supply opening through which toner accommodated in the toner cartridge is supplied into the process cartridge by making use of gravity of the toner.

SUMMARY

In the image forming apparatus where the process cartridge to which the toner cartridge is attached is attached to the housing, a user may dither over the way of replacement of the toner cartridge with a new toner cartridge between two conceivable detachment methods, one method is whether the toner cartridge is accessible to a user to eject the toner cartridge only, and the other method is whether the process cartridge is accessible to a user to eject the process cartridge along with the toner cartridge.

Further, according to a structure where the toner is supplied to the process cartridge from the toner cartridge positioned thereabove through the toner supply opening using gravity, in a case where detachment of only the toner cartridge from the process cartridge is performed while the process cartridge remains in the housing, toner accumulated around the toner supply opening of the toner cartridge may be liable to be leaked outside due to separation of the toner cartridge from the process cartridge with such a posture that the toner supply opening is positioned at a lower end portion of the toner cartridge.

In view of the foregoing, it is an object of the disclosure to provide an image forming apparatus capable of permitting a user to have no hesitation in operation of detachment of the toner cartridge from the process cartridge and avoiding leakage of toner during detachment of the toner cartridge from the process cartridge.

In order to attain the above and other objects, according to one aspect, the disclosure provides an image forming apparatus including a housing and a first process cartridge. The first process cartridge is attachable to and detachable from the housing. The first process cartridge includes a first photosensitive drum, a first developing roller, and a developing frame. The developing frame supports the first developing roller and has a toner inlet opening. The toner cartridge has a toner supply opening. The toner cartridge is positioned above the developing frame such that the toner supply opening and the toner inlet opening face with each other in upward/downward direction. In the state where the first process cartridge to which the toner cartridge is attached is attached to the housing, the toner cartridge is incapable of being detached from the first process cartridge. In a state where the first process cartridge to which the toner cartridge is attached is detached from the housing, the toner cartridge is detachable from the first process cartridge.

BRIEF DESCRIPTION OF THE DRAWINGS

The particular features and advantages of the embodiment(s) as well as other objects will become apparent from the following description taken in connection with the accompanying drawings, in which.

DETAILED DESCRIPTION

Hereinafter, an image forming apparatus 1 according to a first embodiment of the present disclosure will be described with reference to FIGS. 1 through 14.

[Overall Structure of Image Forming Apparatus]

Figure 1:
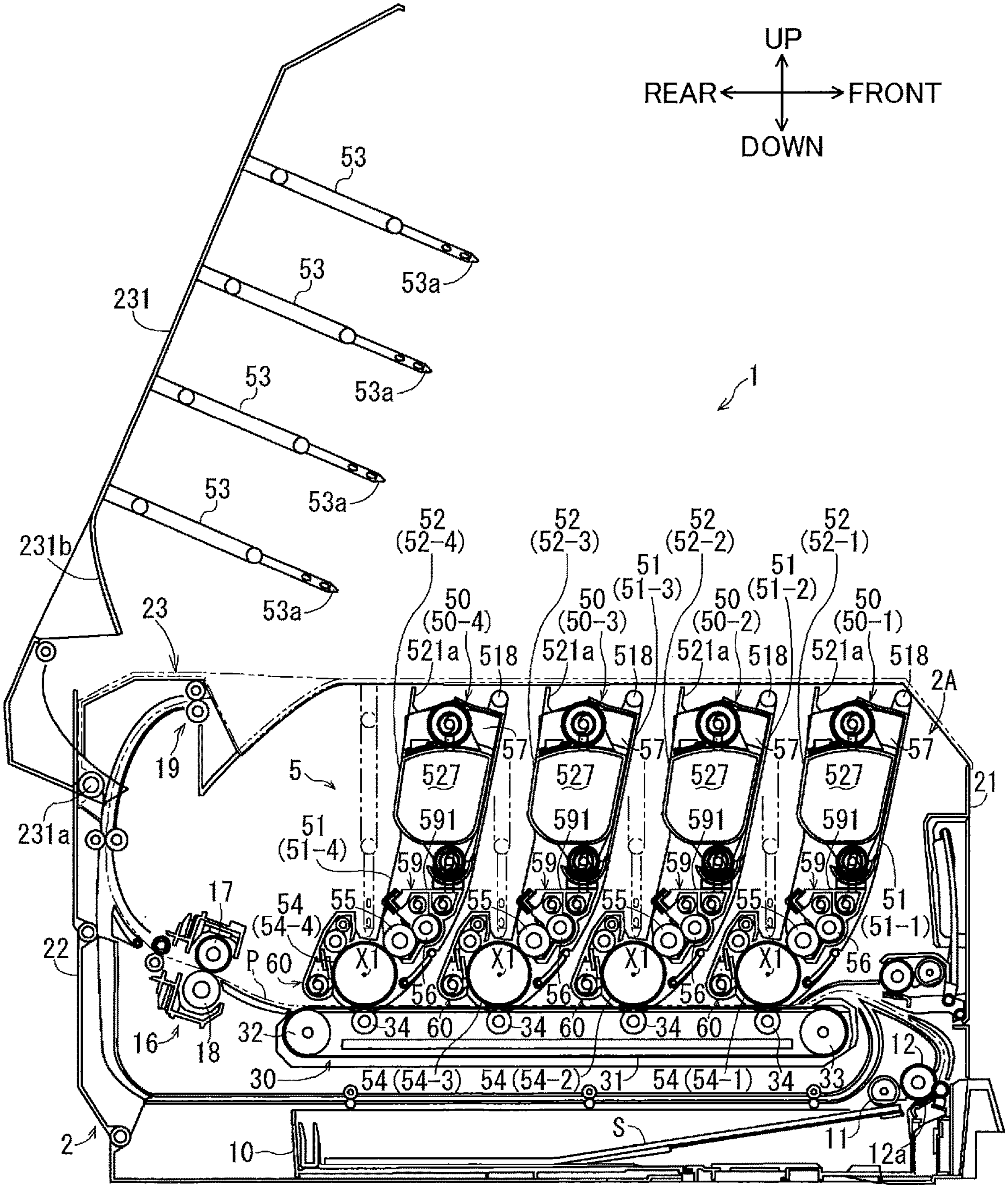
FIG. 1 is a vertical cross-sectional side view of an image forming apparatus according to a first embodiment.
Figure 2:
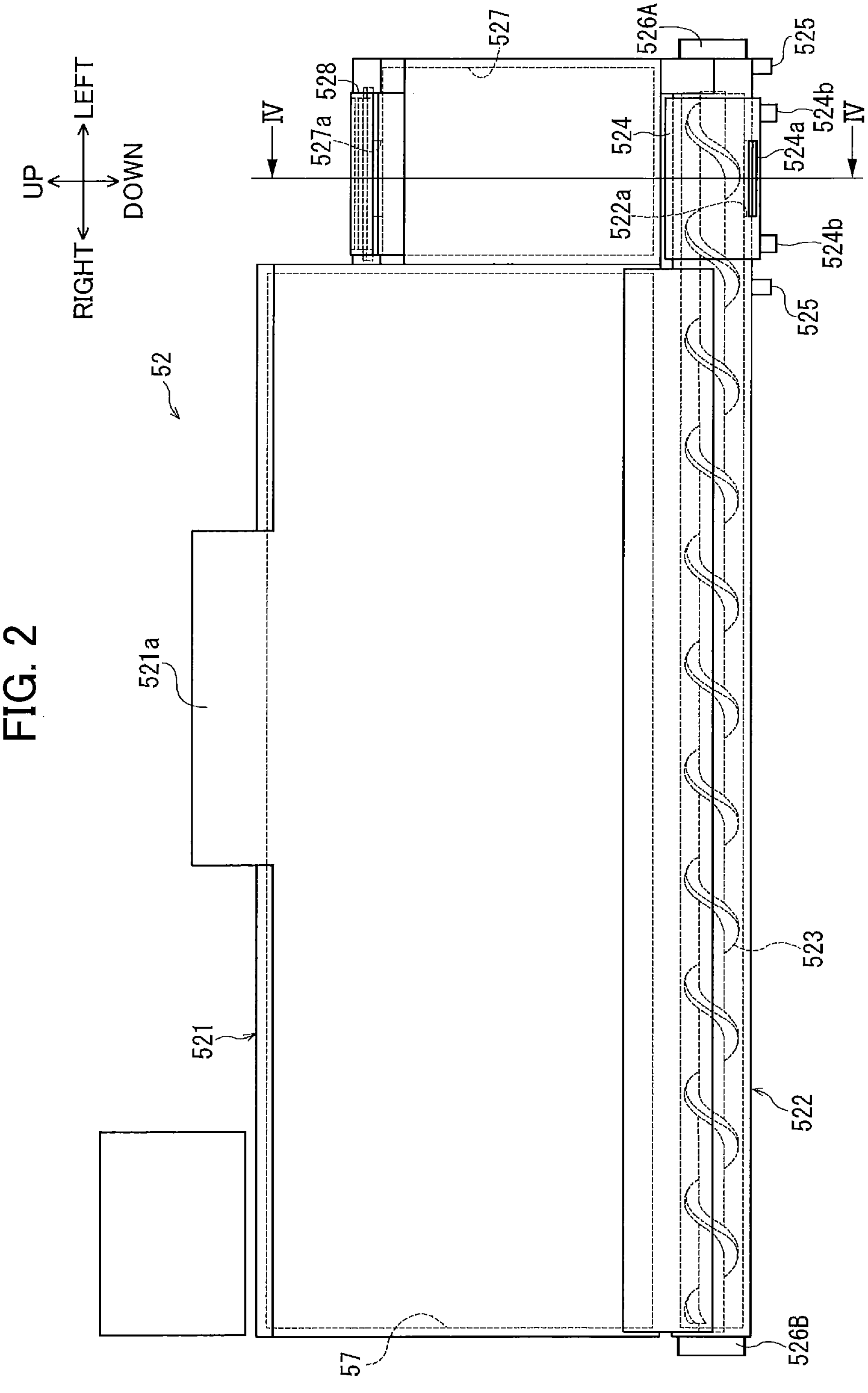
FIG. 2 is a rear view of a toner cartridge in the image forming apparatus according to the first embodiment.
Figure 3:
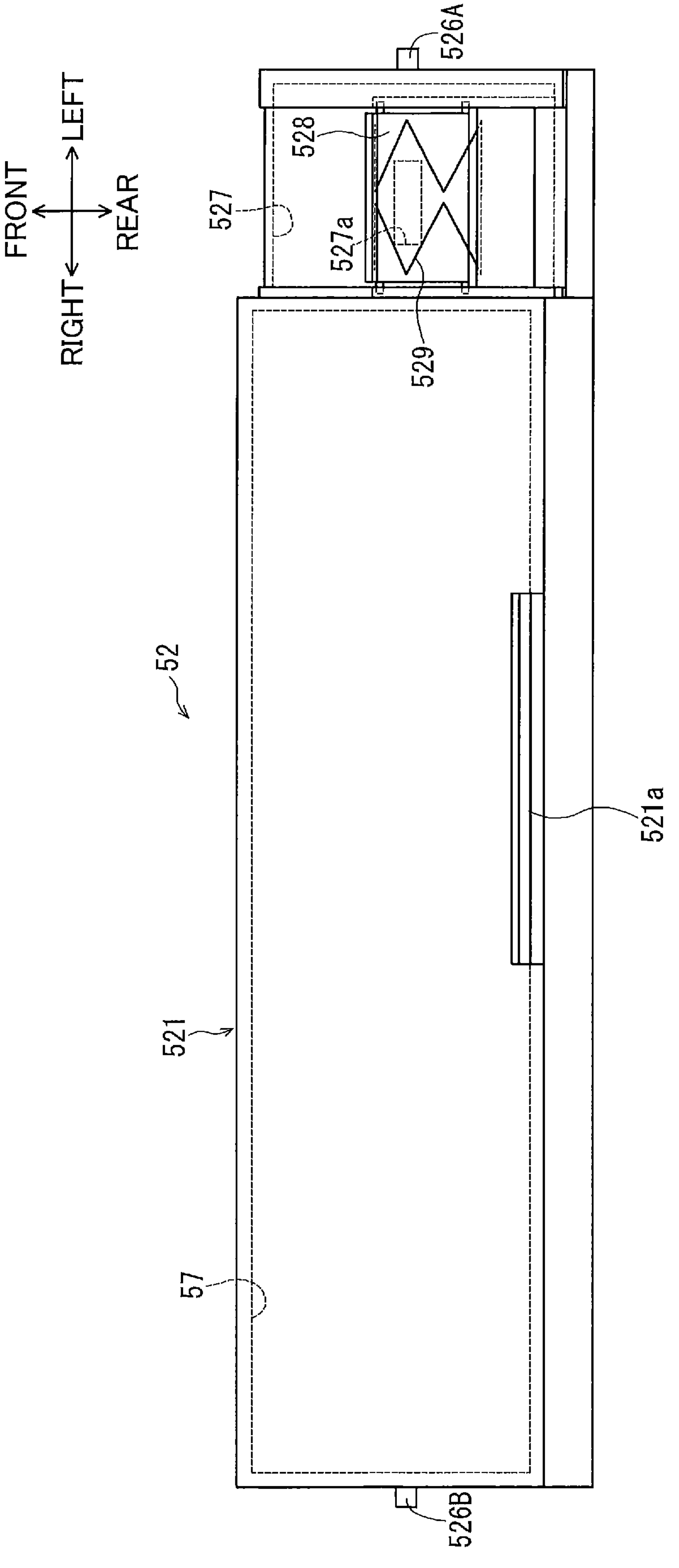
FIG. 3 is a plan view of the toner cartridge.

The image forming apparatus 1 illustrated in FIG. 1 is an electro-photographic type tandem color printer configured to form multiple color image on a sheet S.

In the following description, right side and left side, near side, and far side of the image forming apparatus 1 illustrated in FIG. 1 will be referred to as "front side", "rear side", "left side", and "right side" respectively. Further, upper side, and lower side of the image forming apparatus 1 illustrated in FIG. 1 will be referred to as "upper side" and "lower side".

The image forming apparatus 1 includes a housing 2, a sheet supply tray 10 for supporting the sheet S, and an image forming unit 5 configured to form an image on the sheet S.

The housing 2 has a generally rectangular parallelepiped shape, and accommodates therein the sheet supply tray 10 and the image forming unit 5. The housing 2 has a front wall 21, a rear wall 22, and an upper wall 23. The housing 2 has a rear end and a front end which are examples of one end and another end in frontward/rearward direction, respectively. The rear wall 22 and the front wall 21 are examples of one end wall and another end wall of the housing in frontward rearward direction.

The upper wall 23 is formed with an opening 2A. The housing 2 includes a top cover 231 configured to open and close the opening 2A. The top cover 231 has a rear end portion provided with a pivot shaft 231*a*, and is pivotally movable about an axis of the pivot shaft 231*a* between a closed position where the top cover 231 closes the opening 2A and an open position where the top cover 231 opens the opening 2A. A sheet discharge tray 231*b* sloping diagonally downward and rearward is formed in the top cover 231.

The sheet supply tray 10 is positioned at a lower internal portion of the housing 2, and is configured to be movable in frontward/rearward direction. That is, the sheet supply tray 10 can be pulled frontward from an inward position illustrated in FIG. 1 where the sheet supply tray 10 is at a predetermined sheet supplying position to an outward position or separated position where the sheet supply tray 10 is separated from the housing 2. The sheet supply tray 10 can restore the inward position by being pushed rearward.

A sheet conveying passage P for conveying the sheet S is provided in the housing 2, and extends from the sheet supply tray 10 to the sheet discharge tray 231*b* through the image forming unit 5. Inside the housing 2, a sheet supply roller 11, a separation roller 12, and a separation pad 12*a* are provided. Each one of sheets S supported in the sheet supply tray 10 is separated from remaining sheets, and is delivered to the sheet conveying passage P by the sheet supply roller 11, the separation roller 12 and the separation pad 12*a*.

The image forming unit 5 is positioned above the sheet supply tray 10 and includes four process units 50 arrayed in line in frontward/rearward direction. Each of the process units 50 is attachable to and detachable from the housing 2, and corresponds to the color of black, yellow, magenta, and cyan.

Each process unit 50 includes a process cartridge 51 and a toner cartridge 52. The process cartridge 51 is attachable to and detachable from the housing 2, and the toner cartridge 52 is attachable to and detachable from the process cartridge 51.

The process cartridge 51 includes a photosensitive drum 54, a developing unit 59, a charge roller 63 (see FIG. 8A), and a drum cleaning unit 60. The photosensitive drum 54 is generally hollow cylindrical defining an axial direction extending in leftward/rightward direction. The photosensitive drum 54 is rotatably supported by a frame of the process cartridge 51. The drum cleaning unit 60 includes a cleaning blade 64 (see FIG. 8A).

The developing unit 59 includes a developing roller 55, a supply roller 56, a layer thickness regulation blade 62 (see FIG. 8A), and a developing frame 591 movably supported by the frame of the process cartridge 51. The developing roller 55 extends in leftward/rightward direction, and is rotatably supported by the developing frame 591. The developing roller 55 is in contact with a front upper portion of the photosensitive drum 54. The supply roller 56 extends in leftward/rightward direction, and is rotatably supported by the developing frame 591. The supply roller 56 is in contact with a front upper portion of the developing roller 55.

The toner cartridge 52 includes a toner accommodating portion 57 configured to accommodate therein toner as developing agent. The toner accommodating portion 57 is positioned above the developing unit 59. Toner is supplied from the toner accommodating portion 57 to the supply roller 56 which supplies toner to the developing roller 55. The developing roller 55 supplies toner to the photosensitive drum 54.

The top cover 231 is provided with exposure heads 53 configured to expose surfaces of the photosensitive drums 54 to light. Four exposure heads 53 are provided in one-to-one correspondence with the four photosensitive drums 54. The exposure heads 53 are arrayed in line in frontward/rearward direction. Each exposure head 53 extends downward from the top cover 231, and has a lower end portion provided with a light emitting portion 53*a*. The light emitting portion 53*a* is positioned adjacent to an upper portion of the photosensitive drum 54 in the closed state of the top cover 231. The light emitting portion 53*a* is constituted by an LED array in which a plurality of LED elements are arrayed in line in leftward/rightward direction.

A belt 31 is positioned below and faced with the photosensitive drums 54. The belt 31 is looped between a drive roller 32 and a driven roller 33 positioned frontward of the drive roller 32. Transfer rollers 34 are positioned below the photosensitive drums 54. Each of the transfer rollers 34 and each of the photosensitive drum 54 nip the endless belt 31 therebetween. A combination of the belt 31, the drive roller 32, the driven roller 33, and the transfer rollers 34 constitutes a belt unit 30.

In the image forming unit 5, after the surface of the photosensitive drum 54 is uniformly charged by the charge roller 63, the surface is locally exposed to light by the exposure head 53 on a basis of a predetermined image data. Hence, an electrostatic latent image based on the image data is formed on the surface of the photosensitive drum 54.

On the other hand, toner accommodated in the toner accommodating portion 57 is charged with positive polarity at a position between the supply roller 56 and the developing roller 55, and is carried on the surface of the developing roller 55. Then, the toner carried on the developing roller 55 is supplied to the electrostatic latent image formed on the surface of the photosensitive drum 54, so that toner image is carried on the surface of the photosensitive drum 54.

When the sheet S fed toward the image forming unit 5 from the sheet supply tray 10 is conveyed onto the belt 31, the sheet S is conveyed by the belt 31, and is successively introduced to nipping portions between the belt 31 and the photosensitive drums 54. Each transfer roller 34 is applied with transfer bias. Hence, the toner image on each photosensitive drum 54 is transferred onto the sheet S when the sheet S on the belt 31 is moved past the transfer roller 34. As such, the toner image carried on the photosensitive drum 54 is transferred to the sheet S by means of the belt unit 30.

At this time, toner that has not been transferred to the sheet S may remain on the surface of the photosensitive drum 54. The cleaning blade 64 of the drum cleaning portion 60 is configured to scrape off the residual toner from the surface of the photosensitive drum 54. Hence, the waste toner remaining on the surface of the photosensitive drum 54 is collected in the drum cleaning unit 60.

Incidentally, the belt 31 according to this embodiment is configured to support the sheet S on which toner image is transferred while the sheet S is conveyed on the belt 31. However, as a modification, the belt may be an intermediate transfer belt, such that a toner image may be initially transferred onto the intermediate transfer belt, and then, the toner image on the intermediate transfer belt may be transferred onto the sheet S.

The sheet S on which the toner image is transferred is conveyed to a fixing unit 16 positioned downstream of the image forming unit 5 in a sheet conveying direction. The fixing unit 16 includes a heat roller 17 and a pressure roller 18 in pressure contact with the heat roller 17. The toner image on the sheet S is thermally fixed to the sheet S when the sheet S is moved along a portion between the heat roller 17 and the pressure roller 18.

The sheet S on which the toner image is fixed is conveyed from the fixing unit 16 in the downstream direction of the sheet conveying direction, and the sheet S is further conveyed by a discharge roller 19 and is discharged onto the sheet discharge tray 231*b*.

[Toner Cartridge]

As illustrated in FIGS. 2 through 6, the toner cartridge 52 includes a toner cartridge casing 521. The toner cartridge casing 521 defines the toner accommodating portion 57 configured to accommodate therein toner.

The toner cartridge casing 521 has an upper end portion provided with a toner cartridge handle 521*a* which is gripped by a user for detaching the toner cartridge 52 from the process cartridge 51. The toner cartridge handle 521*a* is positioned at a rear end portion of the toner cartridge casing 521 in frontward/rearward direction in a state where the process cartridge 51 is attached to the housing 2, and the toner cartridge 52 is attached to the process cartridge 51.

A connecting portion 522 is provided below the toner accommodating portion 57 of the toner cartridge casing 521. The connecting portion 522 is connectable to the process cartridge 51 in a process of attachment of the toner cartridge 52 to the process cartridge 51. In the toner cartridge 52, toner accommodated in the toner accommodating portion 57 can be supplied to the supply roller 56 of the process cartridge 51 through the connecting portion 522.

The toner accommodating portion 57 is in communication with an interior of the connecting portion 522, so that toner accommodated in the toner accommodating portion 57 can flow into the connecting portion 522. A screw feeder 523 is provided inside the connecting portion 522. The screw feeder 523 has a rotation axis extending in leftward/rightward direction, and is configured to convey toner introduced in the connecting portion 522 leftward.

The connecting portion 522 has a lower portion having an arcuate shape protruding downward in side view. The lower end portion of the connecting portion 522 has a left end portion formed with a toner supply opening 522*a* through which toner is configured to pass. The toner supply opening 522*a* is in a form of an elongated slot extending in leftward/rightward direction.

The toner cartridge 52 further includes a toner cartridge shutter 524 configured to open and close the toner supply opening 522*a*. The toner cartridge shutter 524 is positioned at the left end portion of the connecting portion 522. The toner cartridge shutter 524 has a generally hollow cylindrical shape having an axis. The toner cartridge shutter 524 is disposed over the connecting portion 522 with a posture such that the axis of the toner cartridge shutter 524 extends in leftward/rightward direction. The toner cartridge shutter 524 is formed with an elongated slot as a communication opening 524*a* extending in leftward/rightward direction. The communication opening 524*a* has a size in conformance with that of the toner supply opening 522*a*.

Figure 4B:
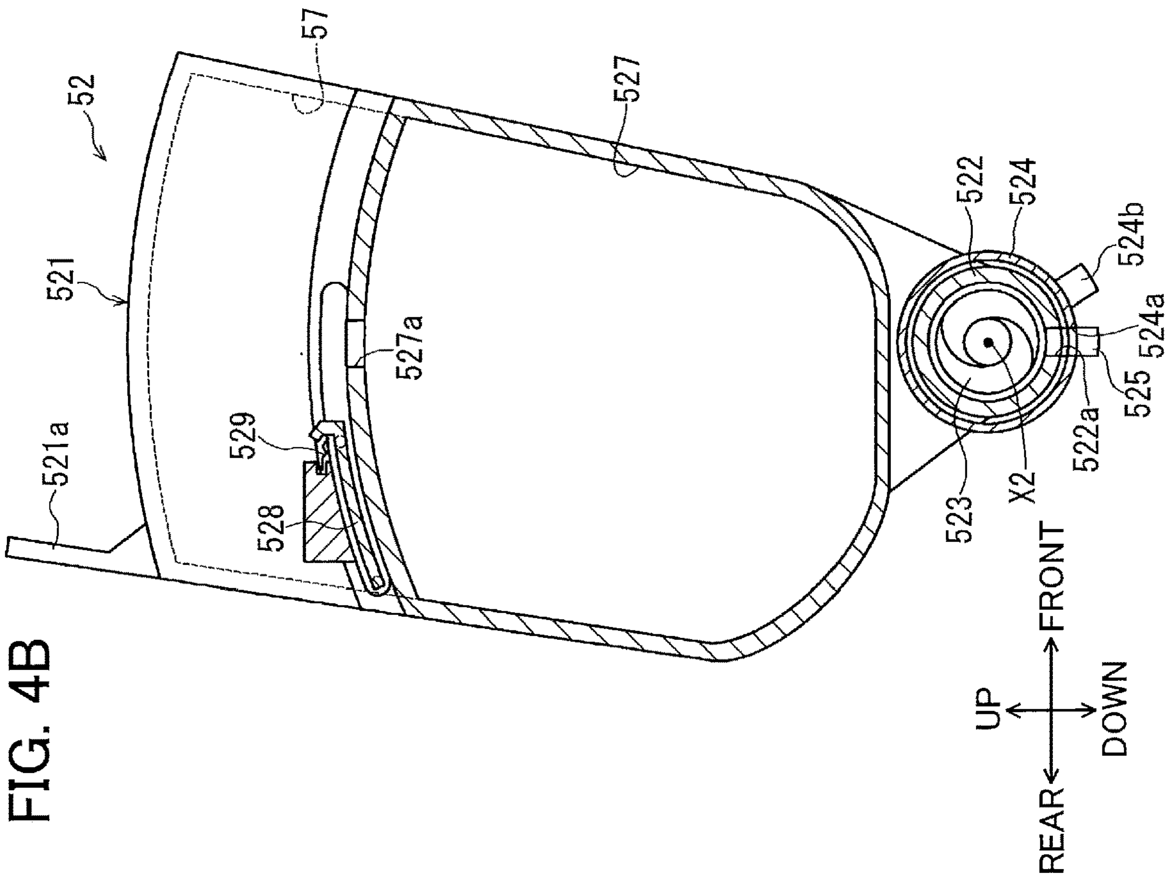
FIG. 4B is a cross-sectional view of the toner cartridge taken along the line IV-IV in FIG. 2, and particularly illustrates a state where the toner cartridge shutter and the inlet shutter are open.

A pair of first protruding portions 524*b* protrudes downward from the toner cartridge shutter 524 at positions outward of the toner supply opening 522*a* of the connecting portion 522 in leftward/rightward direction. As illustrated in FIG. 4B, a position of the first protruding portion 524*b* is different from the position of the communication opening 524*a* in a circumferential direction of the toner cartridge shutter 524. That is, the communication opening 524*a* is positioned rearward of the first protruding portion 524*b* in the circumferential direction.

A pair of second protruding portions 525 protrudes downward from the lower end portion of the connecting portion 522 at positions outward of the toner cartridge shutter 524 in leftward/rightward direction. Positions of the second protruding portions 525 and the position of the toner supply opening 522*a* are coincident with each other in the circumferential direction of the connecting portion 522.

A guide rib 526A having a rectangular shape protrudes leftward from the left end of the connecting portion 522 and extends in upward/downward direction. A guide rib 526B having a rectangular shape protrudes rightward from the right end of the connecting portion 522 and extends in upward/downward direction.

The toner cartridge shutter 524 is angularly rotatable relative to the connecting portion 522 of the toner cartridge casing 521 about the axis of the toner cartridge shutter 524. Hence, the toner cartridge shutter 524 is movable between a closed position where the toner cartridge shutter 524 closes the toner supply opening 522*a* and an open position where the toner cartridge shutter 524 opens the toner supply opening 522*a*.

Figure 4A:
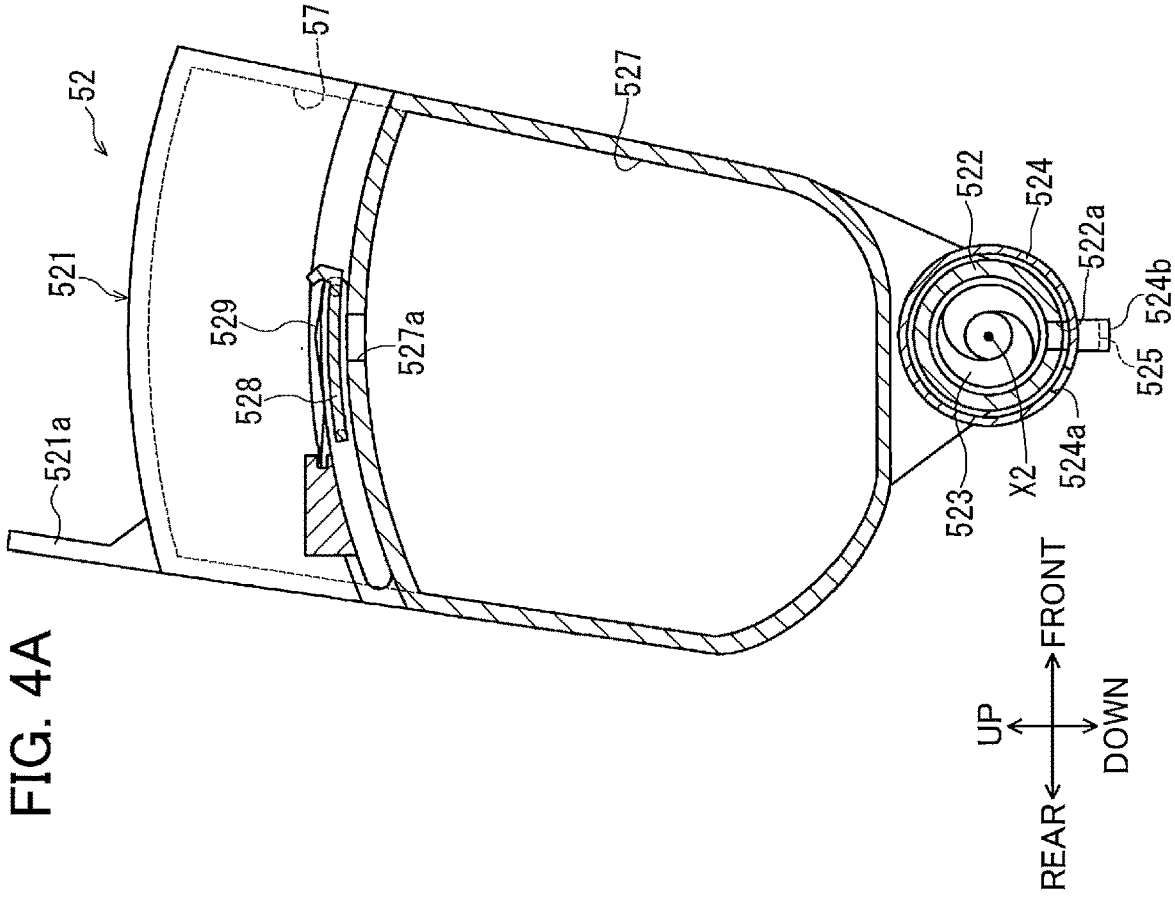
FIG. 4A is a cross-sectional view of the toner cartridge taken along the line IV-IV in FIG. 2, and particularly illustrates a state where a toner cartridge shutter and an inlet shutter are closed.
Figure 5A:
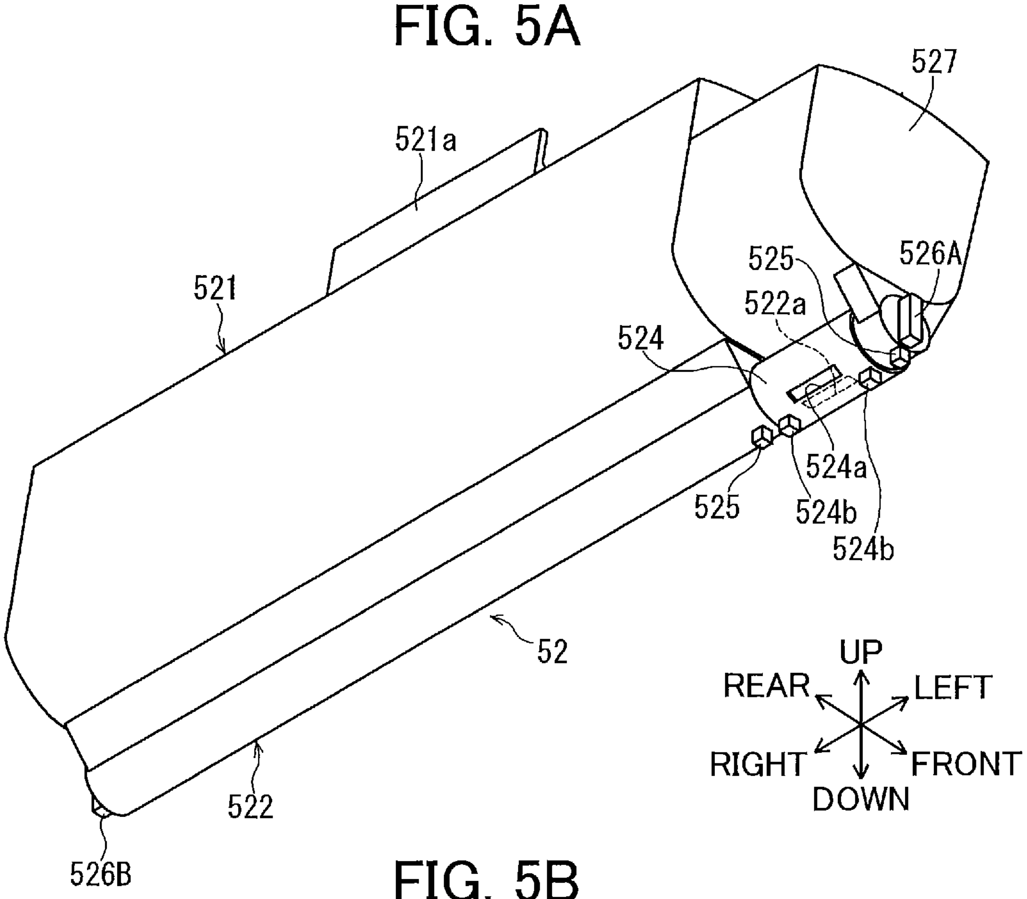
FIG. 5A is a perspective view of the toner cartridge as viewed from diagonally below the toner cartridge, and particularly illustrates a state where the toner cartridge shutter is closed.

For example, as illustrated in FIGS. 4A and 5A, the toner supply opening 522*a* is closed by the toner cartridge shutter 524 in a case where the angular rotational position of the toner cartridge shutter 524 permits the communication opening 524*a* of the toner cartridge shutter 524 to be offset from the toner supply opening 522*a* of the connecting portion 522 in the circumferential direction.

The toner cartridge shutter 524 is at the closed position when the toner supply opening 522*a* is closed by the toner cartridge shutter 524. In this case, angular position of the first protruding portions 524*b* of the toner cartridge shutter 524 is coincident with the position of the second protruding portions 525 in the circumferential direction.

Figure 5B:
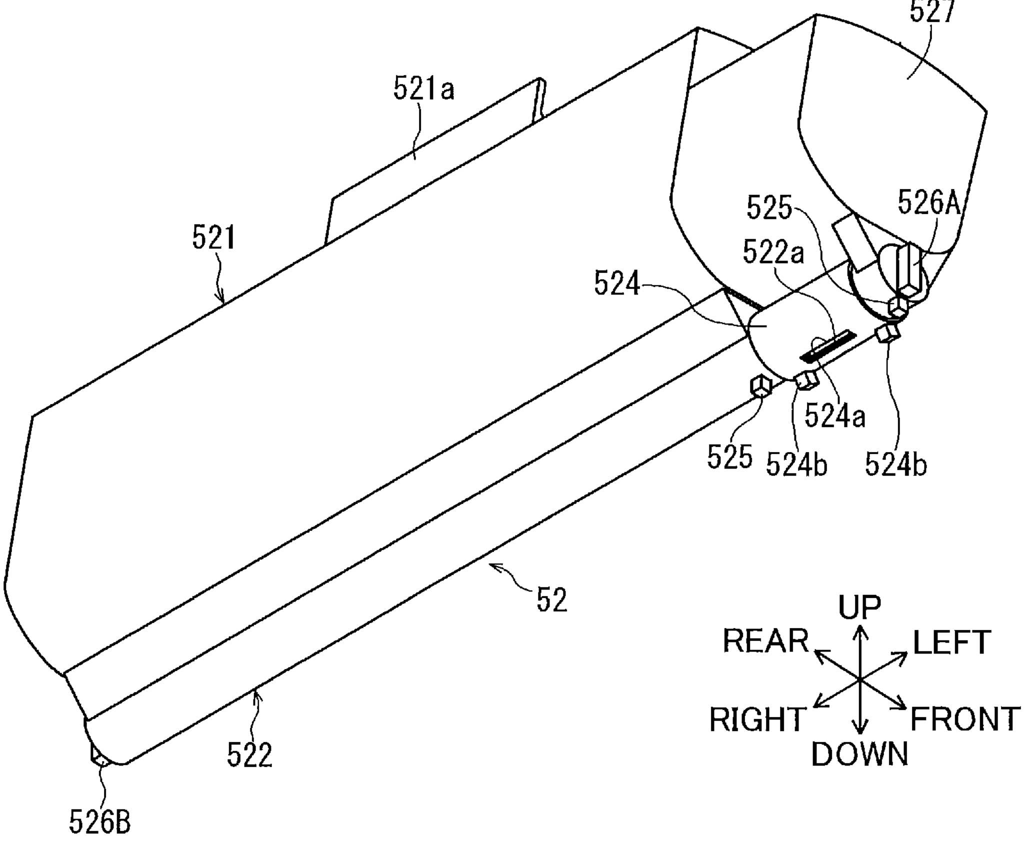
FIG. 5B is a perspective view of the toner cartridge as viewed from diagonally below the toner cartridge, and particularly illustrates a state where the toner cartridge shutter is open.
Figure 6:
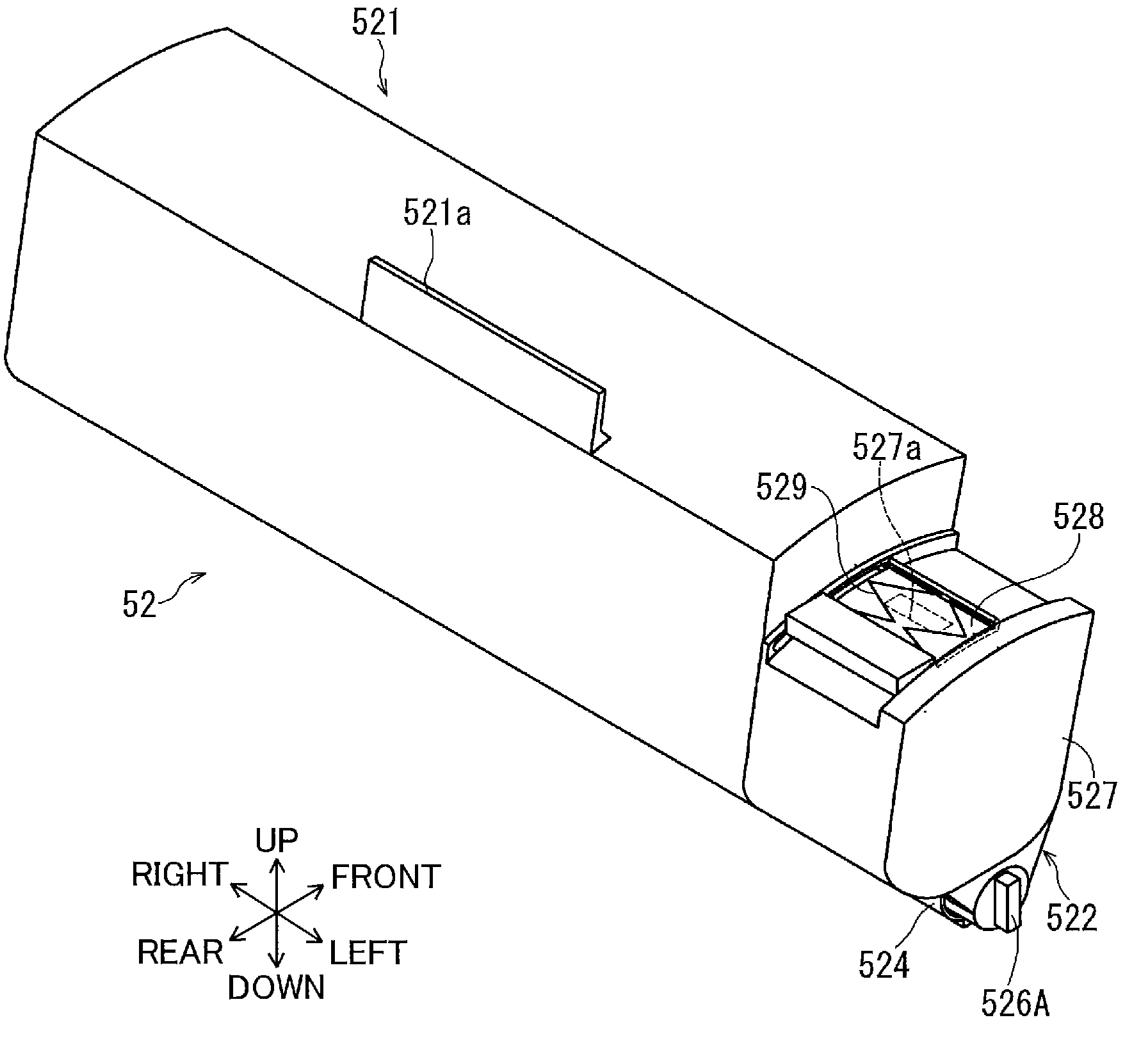
FIG. 6 is a perspective view of the toner cartridge as viewed from diagonally above the toner cartridge, and particularly illustrates a state where the inlet shutter is closed.

Further, as illustrated in FIGS. 4B and 5B, the toner supply opening 522*a* is opened by the toner cartridge shutter 524 in a case where the angular rotational position of the toner cartridge shutter 524 permits the communication opening 524*a* of the toner cartridge shutter 524 to be coincide with the toner supply opening 522*a* of the connecting portion 522 in the circumferential direction. In this state, the toner supply opening 522*a* is in communication with the communication opening 524*a*, so that the toner supply opening 522*a* is opened by the toner cartridge shutter 524.

The toner cartridge shutter 524 is at the open position when the toner supply opening 522*a* is opened by the toner cartridge shutter 524. In this case, angular position of the first protruding portion 524*b* is different from the position of the second protruding portions 525 of the connecting portion 522 in the circumferential direction. The first protruding portion 524*b* is positioned frontward of the second protruding portion 525.

In this way, in the toner cartridge 52, opening and closing of the toner supply opening 522*a* by the toner cartridge shutter 524 can be performed by angularly rotating the toner cartridge shutter 524 relative to the connecting portion 522 to change the angular position of the toner cartridge shutter 524 relative to the connecting portion 522.

The toner cartridge casing 521 includes a waste toner retaining portion 527 configured to retain waste toner collected from the surface of the photosensitive drum 54 by the drum cleaning unit 60. The waste toner retaining portion 527 is positioned leftward of the toner accommodating portion 57 and above the toner cartridge shutter 524.

The waste toner retaining portion 527 has an upper wall formed with an inlet opening 527*a* for introducing the waste toner to an interior of the waste toner retaining portion 527. The toner cartridge 52 includes an inlet opening shutter 528 configured to open and close the inlet opening 527*a*. The inlet opening shutter 528 is positioned above the waste toner retaining portion 527.

The inlet opening shutter 528 is movable in frontward/rearward direction between a closing position as illustrated in FIG. 4A where the inlet opening shutter 528 closes the inlet opening 527*a* and an opening position rearward of the closing position as illustrated in FIG. 4B where the inlet opening shutter 528 opens the inlet opening 527*a*.

The toner cartridge 52 further includes an urging member such as a spring 529 normally urging the inlet opening shutter 528 toward the closing position. The spring 529 is positioned above the inlet opening shutter 528. The inlet opening shutter 528 is movable to the closing position by the urging force of the spring 529. The inlet opening shutter 528 is configured to move rearward to the opening position against the urging force of the spring 529.

[Process Cartridge]

(Side Frame)

Figure 7:
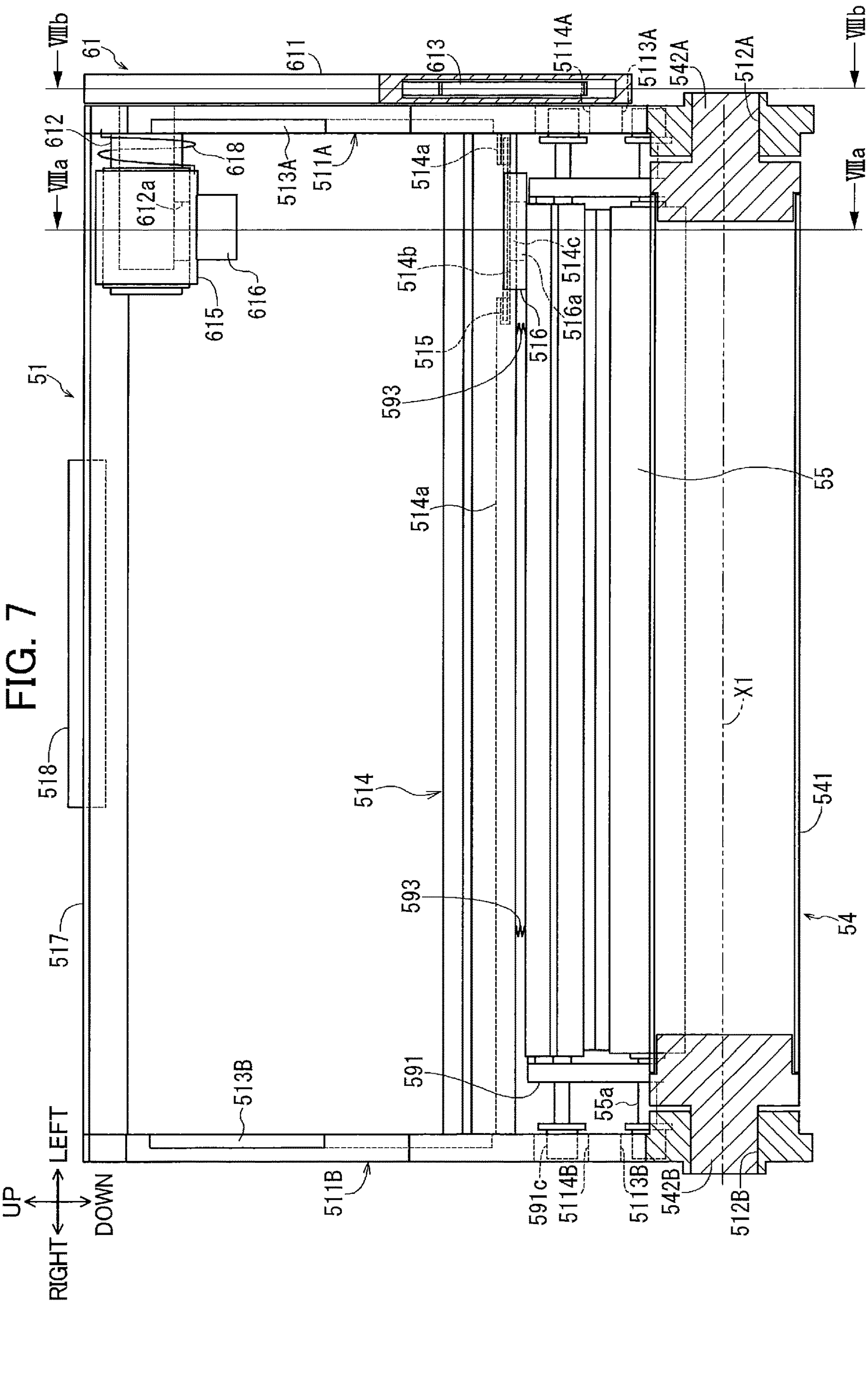
FIG. 7 is a cross-sectional view of a process cartridge taken alone a plane passing through a rotation axis of a photosensitive drum in the image forming apparatus according to the first embodiment.
Figure 8B:
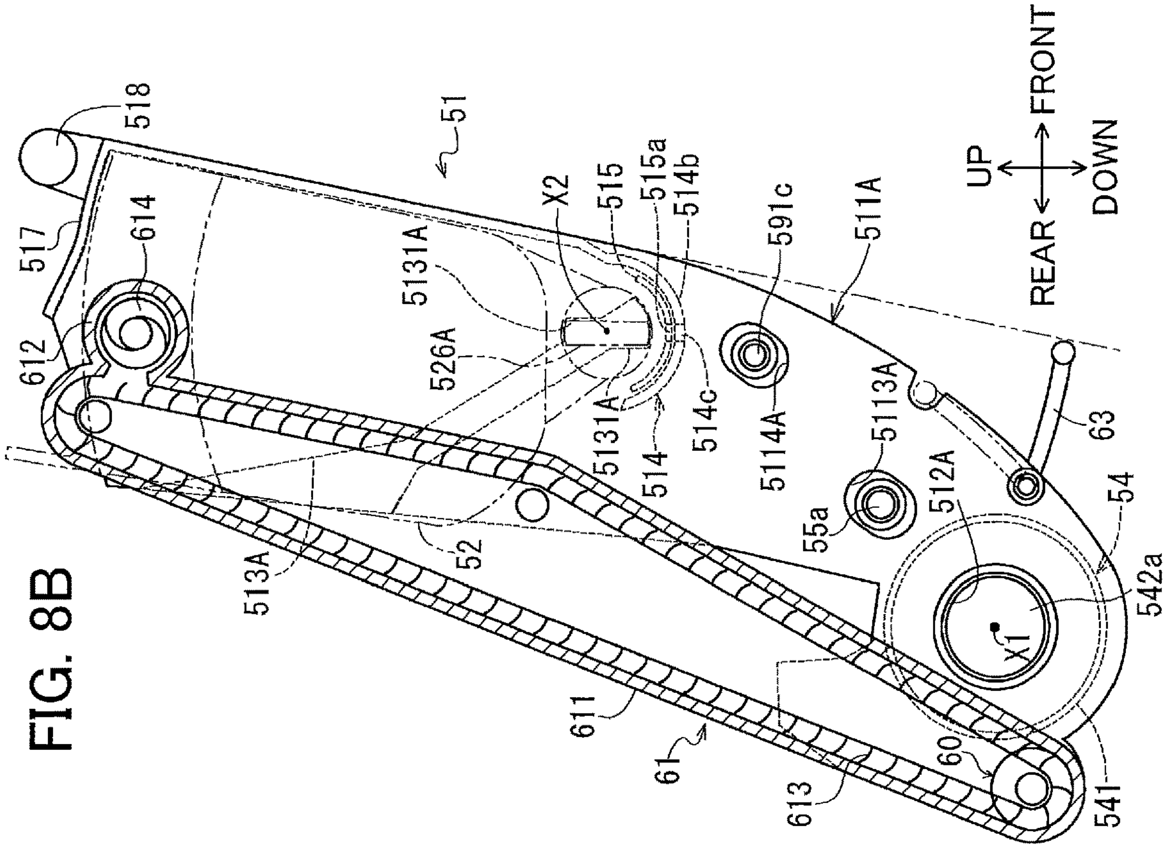
FIG. 8B is a cross-sectional view taken along the line VIIIb-VIIIb in FIG. 7.
Figure 8A:
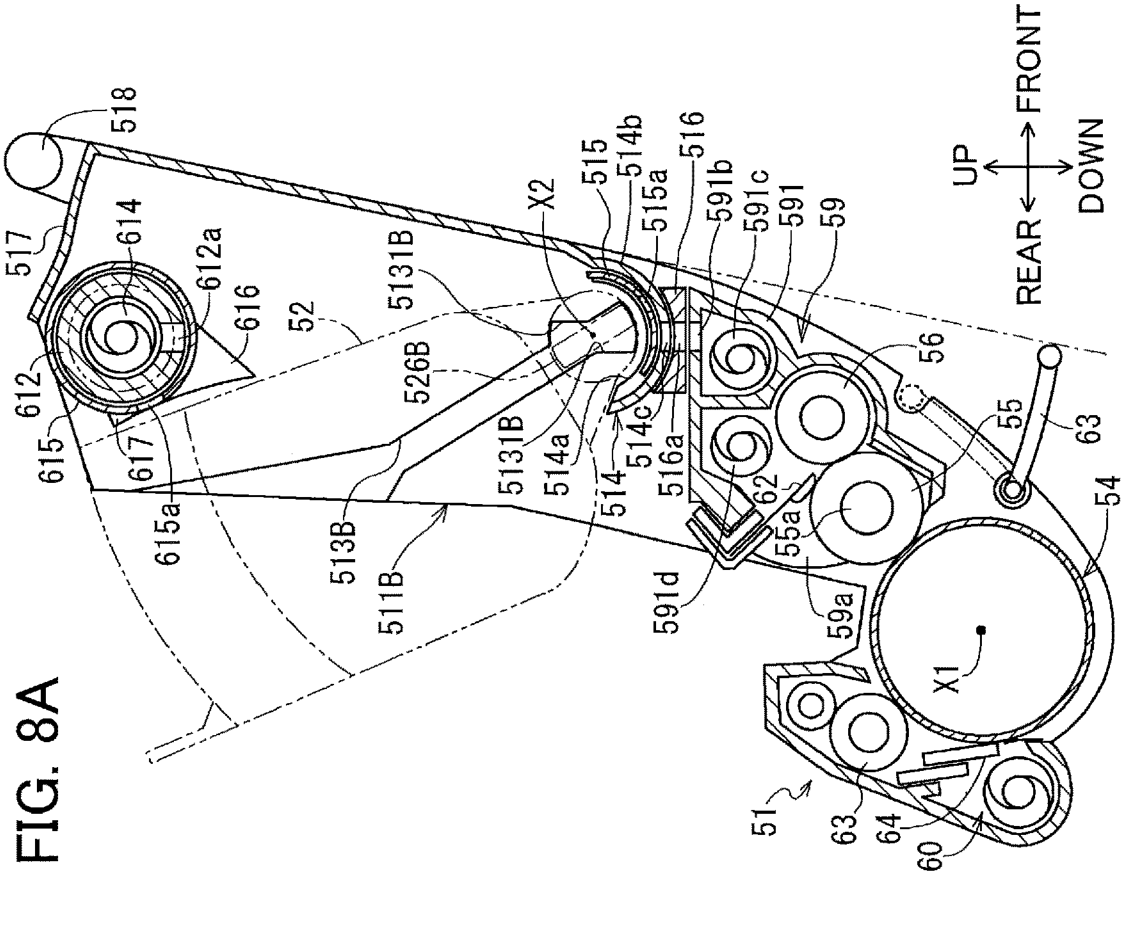
FIG. 8A is a cross-sectional view taken along the line VIIIa-VIIIa in FIG. 7.
Figure 9:
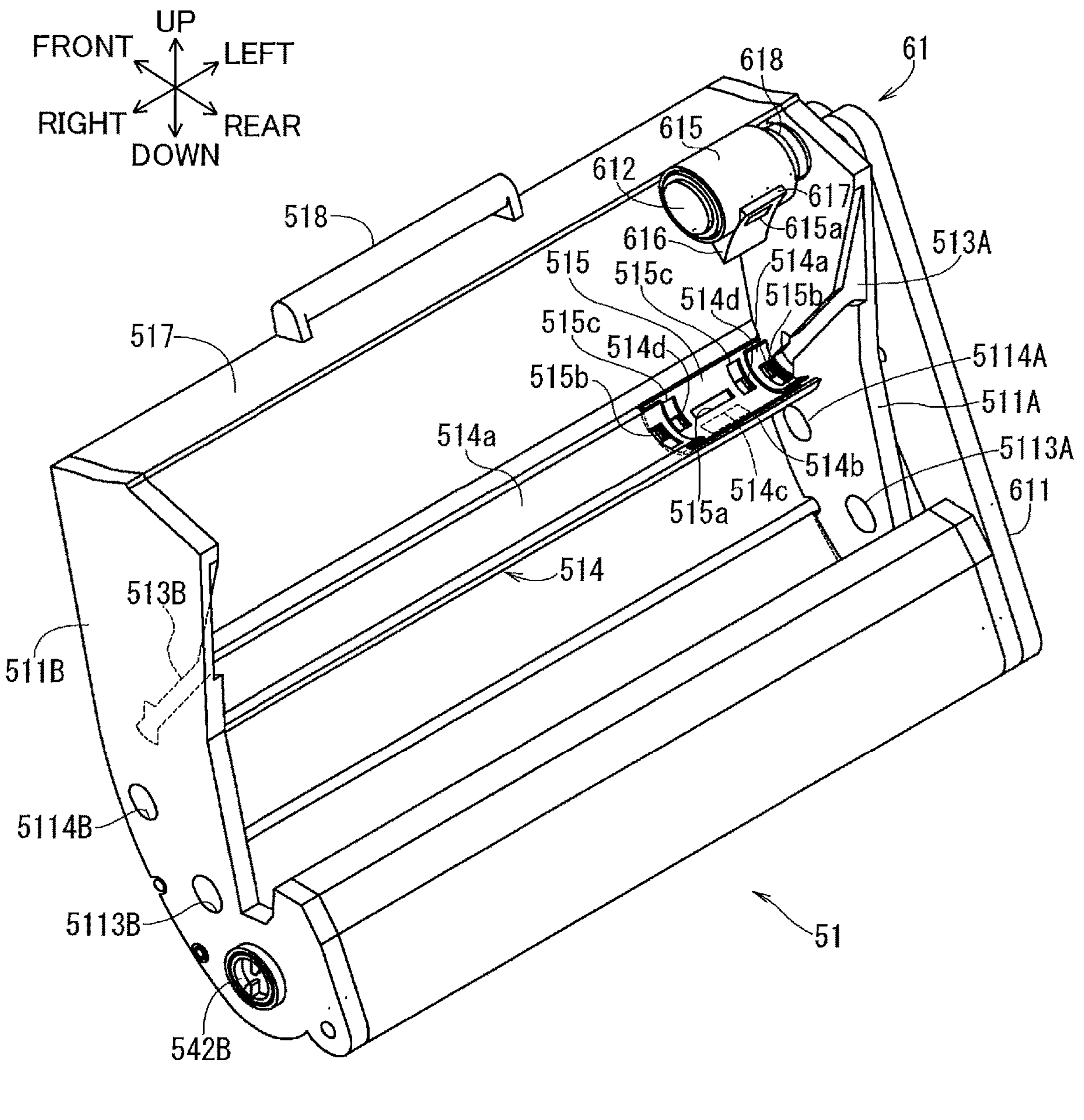
FIG. 9 is a perspective view of the process cartridge.
Figure 10:
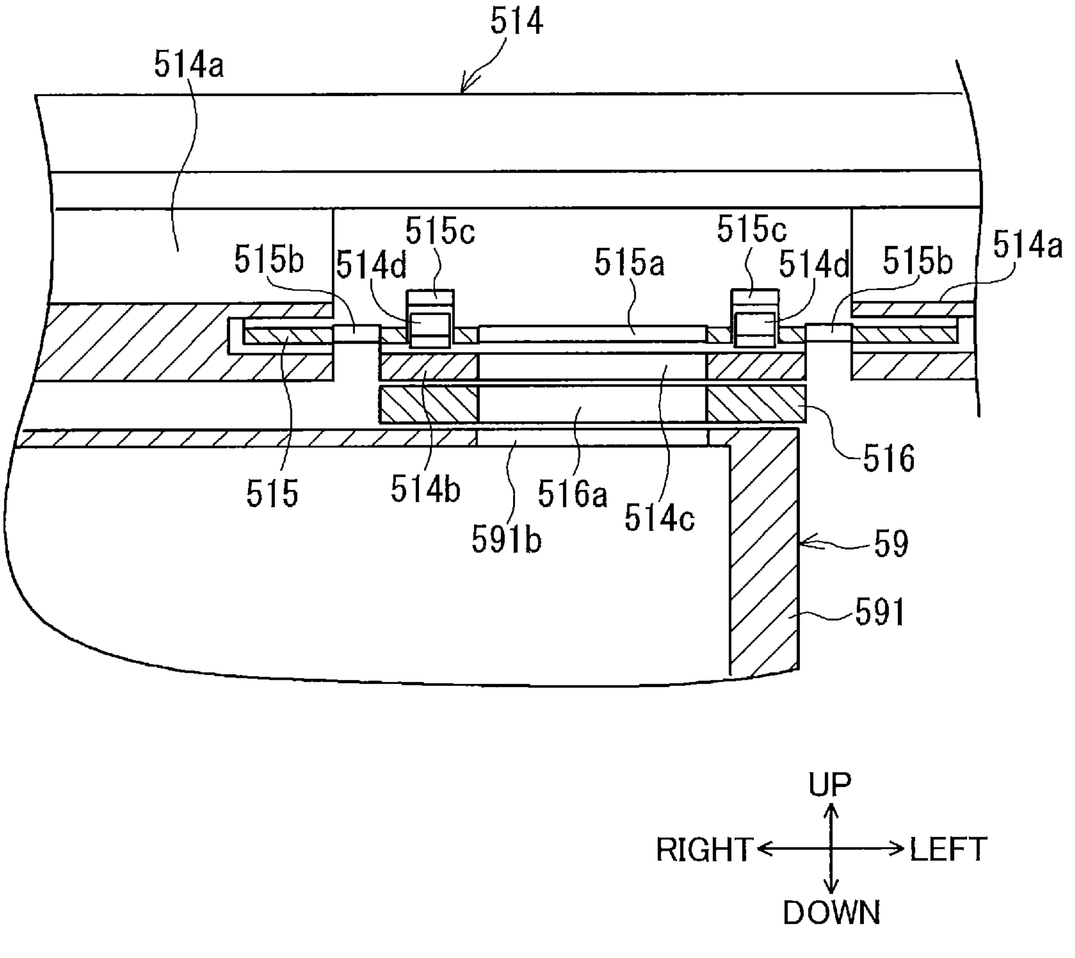
FIG. 10 is a cross-sectional rear view of the process cartridge particularly illustrating a toner inlet opening and its ambient portion.

As illustrated in FIGS. 7 through 9, the process cartridge 51 of the process unit 50 includes a first side frame 511A and a second side frame 511B those supporting the photosensitive drum 54.

The photosensitive drum 54 is rotatable about a rotation axis X1 extending in leftward/rightward direction. Leftward/rightward direction in the housing 2 is an example of a direction of the rotation axis X1 of the photosensitive drum 54 (axial direction of the photosensitive drum 54). Frontward/rearward direction in the housing 2 is an example of a first direction perpendicular to the direction of the rotation axis X1, a rear end of the housing 2 is an example of one end in the first direction, and a front end of the housing 2 is an example of another end in the first direction opposite to the one end.

The photosensitive drum 54 includes a drum body 541, a drum shaft 542A protruding leftward from the drum body 541, and a drum shaft 542B protruding rightward from the drum body 541. The drum shaft 542A constitutes a first end of the photosensitive drum 54 in the direction of the rotation axis X1, and the drum shaft 542B constitutes a second end of the photosensitive drum 54 in the direction of the rotation axis X1.

The first side frame 511A extends in a vertical direction perpendicular to the direction of the rotation axis X1, and rotatably supports the drum shaft 542A. The second side frame 511B extends in the vertical direction perpendicular to the direction of the rotation axis X1, and rotatably supports the drum shaft 542B.

The first side frame 511A is formed with a support hole 512A rotatably supporting the drum shaft 542A, and the second side frame 511B is formed with a support hole 512B rotatably supporting the drum shaft 542B.

Since the drum shafts 542A and the 542B are rotatably supported by the support holes 512A, 512B, respectively, the photosensitive drum 54 is rotatable about the rotation axis X1.

As illustrated in FIGS. 7 through 10, the process cartridge 51 includes a first connection frame 517 and a second connection frame 514 for connecting the first side frame 511A and the second side frame 511B to each other.

The first connection frame 517 extends in leftward/rightward direction and constitutes an upper end portion of the process cartridge 51. The first connection frame 517 is spanned between the first side frame 511A and the second side frame 511B.

The first connection frame 517 is positioned above the toner cartridge 52 attached to the process cartridge 51. That is, in a state where the process cartridge 51 is attached to the housing 2 and the toner cartridge 52 is attached to the process cartridge 51, the first connection frame 517 is positioned opposite to the photosensitive drum 54 with respect to the toner cartridge 52 in upward/downward direction.

The process cartridge 51 includes a process cartridge handle 518 protruding upward from a front end portion of the first connection frame 517. The process cartridge handle 518 is a hand grip configured to be gripped by a user when the process cartridge 51 is to be detached from the housing 2.

The second connection frame 514 extends in leftward/rightward direction and is spanned between the first side frame 511A and the second side frame 511B at an intermediate position of the process cartridge 51 in upward/downward direction.

The second connection frame 514 has a left end, which is one end of the second connection frame 514 in the direction of the rotation axis X1, connected to the first side frame 511A, and has a right end, which is another end of the second connection frame 514 in the direction of the rotation axis X1, connected to the second side frame 511B. The second connection frame 514 is positioned below the toner cartridge 52 attached to the process cartridge 51.

The second connection frame 514 includes a pair of support surface portions 514*a* and an opening/closing surface portion 514*b*. The opening/closing surface portion 514*b* is positioned at a left portion of the second connection frame 514. One of the support surface portions 514*a*, which is a left second connection frame 514, extends from a left end portion of the opening/closing surface portion 514*b* to a left end portion of the second connection frame 514, and remaining one of the support surface portions 514*a*, which is a right second connection frame 514, extends from a right end portion of the opening/closing surface portion 514*b* to a right end portion of the second connection frame 514. The opening/closing surface portion 514*b* is positioned between the pair of support surface portions 514*a*, i.e., between the left and right second connection frames 514 in leftward/rightward direction.

The support surface portions 514*a* are configured to attachably and detachably support the toner cartridge casing 521 of the toner cartridge 52 attached to the process cartridge 51. In a state of supporting the toner cartridge 52 by the support surface portions 514, the toner cartridge 52 is at a posture where the toner accommodating portion 57 is positioned above the connecting portion 522.

The support surface portion 514*a* has an arcuate shape protruding downward in side view which is in conformance with the shape of the lower portion of the connecting portion 522. The opening/closing surface portion 514*b* positioned between the pair of support surface portions 514*a* has an arcuate shape protruding downward in side view. The arcuate shape has a radius greater than that of the arcuate shape of the support surface portion 514*a*.

The opening/closing surface portion 514*b* is formed with a toner inlet opening 514*c* having a shape of an elongated slot extending in leftward/rightward direction. The toner inlet opening 514*c* has a size corresponding to that of the toner supply opening 522*a* of the connecting portion 522. The toner inlet opening 514*c* is configured to allow toner supplied through the toner supply opening 522*a* of the toner cartridge 52 to pass through the toner inlet opening 514*c*, and is in communication with the interior of the developing frame 591.

The opening/closing surface portion 514*b* is formed with a pair of first recessed portions 514*d* at positions outward of the toner inlet opening 514*c* in leftward/rightward direction. Each first recessed portions 514*d* is configured to be engaged with each first protruding portion 524*b* of the toner cartridge shutter 524 upon attachment of the toner cartridge 52 to the process cartridge 51.

The first recessed portion 514*d* has a shape and a size corresponding to those of the first protruding portion 524*b*. Position of the first recessed portion 514*d* is different from a position of the toner inlet opening 514*c* in a circumferential direction of the second connection frame 514. That is, the toner inlet opening 514*c* is positioned rearward of the first recessed portions 514*d* in the circumferential direction.

The process cartridge 51 includes a process cartridge shutter 515 configured to open and close the toner inlet opening 514*c* of the second connection frame 514. The process cartridge shutter 515 is positioned above the opening/closing surface portion 514*b*.

The process cartridge shutter 515 has an arcuate shape protruding downward in side view. The process cartridge shutter 515 has a left end portion and a right end portion those slidably movably supported in the circumferential direction by the support surface portions 514*a*. Hence, the process cartridge shutter 515 is slidably movable relative to the opening/closing surface portion 514*b* in the circumferential direction.

The process cartridge shutter 515 is formed with a communication opening 515*a* having a shape of an elongated slot extending in leftward/rightward direction. The communication opening 515*a* has a size corresponding to the size of the toner supply opening 522*a* of the connecting portion 522. The process cartridge shutter 515 is formed with a pair of second recessed portions 515*b* at positions outward of the communication opening 515*a* in leftward/rightward direction.

Each second recessed portion 515*b* is configured to be engaged with each second protruding portion 525 of the toner cartridge 52 upon attachment of the toner cartridge 52 to the process cartridge 51. The second recessed portion 515*b* has a shape and a size corresponding to those of the second protruding portion 525. Position of the second recessed portion 515*b* is coincident with a position of the communication opening 515*a* in the circumferential direction.

The process cartridge shutter 515 is formed with a pair of insertion holes 515*c* each being positioned between the communication opening 515*a* and each second recessed portion 515*b* in leftward/rightward direction. The insertion hole 515*c* has a shape of an elongated slot extending in the circumferential direction. Each first protruding portions 524*b* of the toner cartridge shutter 524 is insertable through each insertion hole 515*c*.

The insertion hole 515*c* is at a position in alignment with the first recessed portions 514*d* of the opening/closing surface portion 514*b*, so that the first protruding portion 524*b* can be engaged with the first recessed portion 514*d* while the first protruding portion 524*b* extends through the insertion hole 515*c*. The insertion hole 515*c* has a length in the circumferential direction greater than that of the first protruding portion 524*b*. Hence, the process cartridge shutter 515 is slidably movable in the circumferential direction while the first protruding portion 524*b* extending through the insertion hole 515*c* is engaged with the first recessed portion 514*d*.

The process cartridge shutter 515 is movable between a closing position where the process cartridge shutter 515 closes the toner inlet opening 514*c* of the second connection frame 514 and an opening position where the process cartridge shutter 515 opens the toner inlet opening 514*c* by the sliding movement of the process cartridge shutter 515 relative to the second connection frame 514 in the circumferential direction.

For example, as illustrated in FIG. 8A, the toner inlet opening 514*c* is closed by the process cartridge shutter 515 in a case where the angular rotational position of the process cartridge shutter 515 permits the communication opening 515*a* of the process cartridge shutter 515 to be offset from the toner inlet opening 514*c* of the second connection frame 514 in the circumferential direction.

The process cartridge shutter 515 is at a closed state when the toner inlet opening 514*c* is closed by the process cartridge shutter 515. In this case, a position of the first recessed portions 514*d* of the second connection frame 514 is coincident with the angular position of the second recessed portions 515*b* of the process cartridge shutter 515 in the circumferential direction.

On the other hand, as illustrated in FIG. 10B, the toner inlet opening 514*c* of the connection frame 514 is opened by the process cartridge shutter 515 in a case where the angular rotational position of the process cartridge shutter 515 permits the communication opening 515*a* of the process cartridge shutter 515 to be positioned coincident with the toner inlet opening 514*c* of the second connection frame 514 in the circumferential direction. In this state, the toner inlet opening 514*c* is in communication with the communication opening 515*a*, so that the toner inlet opening 514*c* is opened by the process cartridge shutter 515.

The process cartridge shutter 515 is at an open state when the toner inlet opening 514*c* is opened by the process cartridge shutter 515. In this case, angular position of the second recessed portions 515*b* of the process cartridge shutter 515 is different from the position of the first recessed portions 514*d* of the second connection frame 514 in the circumferential direction. The second recessed portions 515*b* are positioned rearward of the first recessed portions 514*d*.

In this way, in the process cartridge 51, opening and closing of the toner inlet opening 514*c* by the process cartridge shutter 515 can be performed by angularly rotating the process cartridge shutter 515 relative to the second connection frame 514 to change the angular position of the process cartridge shutter 515 relative to the second connection frame 514.

(Guide Groove)

As illustrated in FIGS. 7 through 9, a guide groove 513A is formed in an inner side surface in leftward/rightward direction of the first side frame 511A, and a guide groove 513B is formed in an inner side surface in leftward/rightward direction of the second side frame 511A. These guide grooves 513A, 513B generally extend in upward/downward direction, and inclined diagonally downward and frontward. The guide grooves 513A, 513B are positioned above the second connection frame 514.

The guide grooves 513A, 513B have upper open ends. The guide ribs 526A, 526B of the toner cartridge 52 are insertable in the guide grooves 513A, 513B. The toner cartridge 52 is attachable to the process cartridge 51 by inserting the guide ribs 526A, 526B in the guide grooves 513A, 513B.

The guide ribs 526A, 526B is guided in the guide grooves 513A 513B with their inclined posture such that each lower end of each guide rib is positioned frontward of each upper end of each guide rib when the guide ribs 526A, 526B move along the inclined guide grooves 513A, 513B.

The guide grooves 513A, 513B have lower end portions formed with locking grooves 5131A, 5131B, respectively. Each of the locking grooves 5131A, 5131B has a groove width greater than a groove width of each of the guide grooves 513A, 513B in generally frontward/rearward direction. Further, as illustrated in FIGS. 8A, and 8B, each of the locking grooves 5131A, 5131B has a length in upward/downward direction equal to or slightly greater than a length in upward/downward direction of each of the guide grooves

513A, 513B. Attachment state of the toner cartridge 52 to the process cartridge 51 is provided when the guide ribs 526A, 526B inserted and guided along the guide grooves 513A, 513B reach the lower end portions of the guide grooves 513A, 513B, that is, the locking grooves 5131A, 5131B.

In the attachment state of the toner cartridge 52 to the process cartridge 51, the toner cartridge 52 is pivotally movable relative to the process cartridge 51 about a pivot axis X2 between a second position illustrated in FIG. 8A, and a first position illustrated in FIG. 8B. In the second position, the toner cartridge 52 has an inclined posture such that its upper end portion is positioned rearward of its lower end portion. In the first position, the toner cartridge 52 has a vertical posture by frontward displacement of the upper end portion of the toner cartridge 52 as a result of pivotal frontward movement of the toner cartridge 52 about the pivot axis X2 from the second position.

The pivot axis X2 is an axis of the connecting portion 522, and passes through each of the guide ribs 526A, 526B, and extends in a direction parallel to the rotation axis X1 of the photosensitive drum 54. The first position prevents the toner cartridge 52 from being detached from the process cartridge 51. The second position permits the toner cartridge 52 to be detached from the process cartridge 51.

Specifically, pivotal movement of the guide ribs 526A, 526B relative to the process cartridge 51 is restricted by the guide grooves 513A, 513B until the guide ribs 526A, 526B reach the lower end portions of the guide grooves 513A, 513B. However, the guide ribs 526A, 526B become pivotally movable relative to the process cartridge 51 when the guide ribs 526A, 526B reach the lower end portions, since the locking grooves 5131A, 5131B permit the guide ribs 526A, 526B to be pivotally movable about the pivot axis X2.

Thus, the toner cartridge 52 that is at the second position is pivotally moved to the first position relative to the process cartridge 51. Incidentally, as illustrated in FIG. 8B, the guide ribs 526A, 526B are in abutment with the locking grooves 5131A, 5131B preventing further frontward pivotal movement of the toner cartridge 52 in response to pivotal movement of the toner cartridge 52 from the second position to the first position.

Further, upper surfaces of the guide ribs 526A, 526B are in contact with the locking grooves 5131A, 5131B when the toner cartridge 52 is at the first position. Hence, upward displacement of the toner cartridge 52 relative to the process cartridge 51 is prevented, which prevents the toner cartridge 52 that is at the first position from releasing from the process cartridge 51.

In other words, the second position of the toner cartridge 52 is a position where the toner cartridge 52 can be attached to or detached from the process cartridge 51. The first position of the toner cartridge 52 is a position where the toner cartridge 52 is fixed to the process cartridge 51.

As such, since the toner cartridge 52 is pivotally movably supported by the process cartridge 51 about the pivot axis X2 between the first position where detachment of the toner cartridge 52 from the process cartridge 51 is prevented and the second position where the toner cartridge 52 is detachable from the process cartridge 51, facilitated switching operation between the first position and the second position is attainable by simply pivotally moving the toner cartridge 52 relative to the process cartridge 51.

(Developing Unit)

As illustrated in FIG. 8Am the developing frame 591 of the developing unit 59 includes a developing chamber 59*a* in which the developing roller 55, the layer thickness regulation blade 62, and the supply roller 56 are accommodated. The layer thickness regulation blade 62 is in contact with the surface of the developing roller 55. The supply roller 56 is configured to supply toner to the developing roller 55. The layer thickness regulation blade 62 is configured to regulate a thickness of a toner layer formed on the surface of the developing roller 55 into a predetermined thickness by the contact of the layer thickness regulation blade 62 with the rotating surface of the developing roller 55. The developing roller 55 includes a roller shaft 55*a* protruding outward from the developing frame 591 in leftward/rightward direction (see FIG. 7).

Guide holes 5113A, 5113B are formed in the first side frame 511A and the second side frame 511B, respectively. A left end portion of the roller shaft 55*a* is inserted in the guide hole 5113A, and a right end portion of the roller shaft 55*a* is inserted in the guide hole 5113B. The guide holes 5113A, 5113B are in the form of elongated slots. The roller shaft 55*a* is slidably movable relative to the guide holes 5113A, 5113B in a direction of the elongated direction of the guide holes 5113A, 5113B.

The direction of the major axis of each of the guide holes 5113A, 5113B is coincident with a direction of moving the roller shaft 55*a* of the developing roller 55 toward and away from the photosensitive drum 54. The roller shaft 55*a* is slidably movable within a longitudinal length of the guide holes 5113A, 5113B.

The developing frame 591 is movable in a first direction and a second direction opposite to the first direction by the sliding movement of the roller shaft 55*a* relative to the guide holes 5113A, 5113B. In first direction, the developing roller 55 is brought into pressure contact with the photosensitive drum 54. In the second direction, developing roller 55 moves away from the photosensitive drum 54. An urging member such as a spring 593 is interposed between the developing frame 591 and the second connection frame 514 as illustrated in FIG. 7, so that the developing roller 55 is urged toward the photosensitive drum 54 for the pressure contact.

The developing frame 591 has an upper wall formed with an opening 591*b* having an elongated slot shape extending in leftward/rightward direction. The opening 591*b* is in communication with the interior of the developing frame 591. The opening 591*b* is positioned below the toner inlet opening 514*c* of the opening/closing surface portion 514*b*. The opening 591*b* has a size corresponding to the size of the toner inlet opening 514*c*.

The opening 591*b* and the toner inlet opening 514*c* are overlapped with each other in upward/downward direction, and are communicated with each other. The opening 591*b* and the toner inlet opening 514*c* are configured to allow toner to pass therethrough for supplying toner to the developing unit 59. Toner accommodated in the developing frame 591 can be supplied to the inside of the developing frame 591 through the toner inlet opening 514*c* and the opening 591*b* when the process cartridge shutter 515 is open. Toner can be accommodated in the inside of the developing frame 591.

Screws 591*c*, 591*d* are positioned in the developing frame 591 for supplying toner supplied inside the developing frame 591 to the supply roller 56 positioned in the developing chamber 59*a*. As such, the developing unit 59 has the opening 591*b* for supplying toner to the developing chamber 59*a*.

The screw 591*c* has a longitudinal end portions protruding outward from the developing frame 591 in leftward/rightward direction. The first and second side frames 511A, 511B are formed with guide holes 5114A, 5114B, respectively, in which the longitudinal end portions are inserted. The guide holes 5114A, 5114B have elongated slot shapes extending in a direction parallel to the longitudinal direction of the guide holes 5113A, 5113B. The screw 591*c* is slidably movable relative to the guide holes 5114A, 5114B within the longitudinal length thereof.

Thus, the developing frame 591 is movably supported by the first and second side frames 511A, 511B of the process cartridge 51, since the roller shaft 55*a* is slidably movable relative to the guide holes 5113A, 5113B and the screw 571*c* is slidably movable relative to the guide holes 5114A, 5114B.

As described above, the developing frame 591 is movable relative to the first and second side frames 511A, 511B of the process cartridge 51. Therefore, the developing roller 55 supported by the developing frame 591 is also movable relative to the photosensitive drum 54, thereby stabilizing pressure contacting state of the developing roller 55 with the photosensitive drum 54.

Further, the moving direction of the developing roller 55 together with the developing frame 591 is restricted to the extending direction of the guide holes 5114A, 5114B such that the developing roller 55 is contacted with and separated from the photosensitive drum 54 in the direction. The guide holes 5114A, 5114B can prevents the one of the end portions of the developing roller 55 from being displaced in the circumferential direction of the photosensitive drum 54, thereby maintaining parallelism between the developing roller 55 and the photosensitive drum 54.

Further, as described above, the developing frame 591 is movably supported by the first side frame 511A and the second side frame 511B, the toner inlet opening 514*c* is formed in the second connection frame 514, and the developing frame 591 is formed with the opening 591*b* in communication with the interior of the developing frame 591 and facing the toner inlet opening 514*c*.

With this structure, proper positional relationship suitable for developing operation can be maintained between the developing roller 55 supported by the developing frame 591 of the developing frame 591 and the photosensitive drum 54 supported by the first side frame 511A and the second side frame 511B of the process cartridge 51. Further, if the toner cartridge 52 were attached to the developing frame 591 that is movable relative to the first and second side frames 511A, 511B, operation for attaching the toner cartridge 52 to the movable developing frame 591 may be troublesome. However, according to the first embodiment, the toner cartridge 52 can be attached to the immovable second connection frame 514 fixed to the first and second side frames 511A, 511B by the formation of the toner inlet opening 514*c* in the second connection frame 514. Hence, operation for attaching the toner cartridge 52 to the process cartridge 51 can be facilitated.

(Seal Member)

As illustrated in FIGS. 7 through 8B, a seal member 516 is interposed between an upper surface of the developing frame 591 and the opening/closing surface portion 514*b* of the second connection frame 514. The seal member 516 is formed with a communication opening 516*a* having an elongated slot shape extending in leftward/rightward direction. The communication opening 516*a* has a size corresponding to the size of the toner inlet opening 514*c* of the opening/closing surface portion 514*b*.

The communication opening 516*a* is at a position overlapping with the toner inlet opening 514*c* and the opening 591*b* in upward/downward direction allowing the toner inlet opening 514*c* to communicate with the opening 591*b*.

The seal member 516 is embedded in a space between the upper surface of the developing frame 591 and the opening/closing surface portion 514*b* in upward/downward direction. Since the communication opening 516*a* is formed in the seal member 516, a gap between a peripheral edge portion of the opening portion 591*b* in the upper surface of the developing frame 591 and a peripheral edge portion of the toner inlet opening 514*c* in the opening/closing surface portion 514*b* is embedded by the seal member 516. That is, the seal member 516 is provided between the peripheral edge portions of the opening 591*b* and the toner inlet opening 514*c*.

The seal member 516 is made from elastic material, for example, a sponge, and hence is expandable and shrinkable because of elastic deformation. Accordingly, in spite of change in size of the gap between the developing frame 591 and the opening/closing surface portion 514*b* due to movement of the developing frame 591 relative to the cartridge frame 511, the elastic deformation of the seal member 516 can follow the change in size of the gap, thereby maintaining sealing performance.

Consequently, the seal member 516 can prevent toner moving through the toner inlet opening 514*c* from leaking through the gap between the developing frame 591 and the opening/closing surface portion 514*b*.

(Waste Toner Conveying Unit)

The process cartridge 51 includes a waste toner conveying unit 61 configured to convey waste toner collected from the photosensitive drum 54 by the drum cleaning unit 60 to the waste toner retaining portion 527 of the toner cartridge 52.

Further, the charge roller 63 of the process cartridge 51 is in contact with a rear upper portion of the photosensitive drum 54 (see FIG. 8A). The charge roller 63 is configured to charge the surface of the photosensitive drum 54 by such a contact. The charge roller 63 extends in leftward/rightward direction.

In the process cartridge 51, the surface of the photosensitive drum 54 is locally exposed to light by the exposure head 53 to form an electrostatic latent image on the surface, after the surface is charged by the charge roller 63. A toner image is carried on the surface of the photosensitive drum 54 by supplying toner from the developing roller 55 to the electrostatic latent image. The toner image is transferred to the sheet S by the belt unit 30. At this time, residual toner that has not been transferred to the sheet S remains on the surface of the photosensitive drum 54. Further, foreign particles such as paper dust may be adhered to the surface of the photosensitive drum 54.

As described above, the drum cleaning unit 60 includes the cleaning blade 64 (see FIG. 8A) in contact with the surface of the photosensitive drum 54. The cleaning blade 64 is formed in a flat plate-like member extending in leftward/rightward direction. The cleaning blade 64 has a front lower edge in contact with a rear region of the surface of the photosensitive drum 54. The cleaning blade 64 is configured to scrape residual toner and foreign particles such as paper dust remaining on the surface of the photosensitive drum 54 off the surface.

In the process cartridge 51, after the residual waste toner is scraped off the surface of the photosensitive drum 54 by the cleaning blade 64, the waste toner is collected by the drum cleaning unit 60. The collected waste toner will be conveyed by the waste toner conveying unit 61 to the waste toner retaining portion 527 of the toner cartridge 52.

The waste toner conveying unit 61 includes a vertical conveyance case 611, a horizontal conveyance case 612, a belt conveyer 613, a screw 614, a waste toner conveyance shutter 615, a first abutment segment 616, and a second abutment segment 617.

The vertical conveyance case 611 extends along a left end portion of the frame 511 of the process cartridge 51 from a lower end portion to an upper end portion of the left end portion. The horizontal conveyance case 612 is positioned at an upper left end portion of the frame 511, and is connected to the vertical conveyance case 611. The horizontal conveyance case 612 has a lower end portion formed with a waste toner outlet opening 612*a* through which waste toner is passable.

The belt conveyer 613 is positioned inside the vertical conveyance case 611, and is configured to convey the waste toner collected by the drum cleaning unit 60 positioned at a lower end portion of the vertical conveyance case 611 to an upper end portion of the vertical conveyance case 611. The screw 614 is positioned inside the horizontal conveyance case 612 with such a posture that an axis of the screw 614 extends in leftward/rightward direction. The screw 614 is configured to convey the waste toner conveyed to the upper end portion of the vertical conveyance case 611 by the belt conveyer 613 toward the waste toner outlet opening 612*a*.

The waste toner conveyance shutter 615 is configured to open and close the waste toner outlet opening 612*a*. The waste toner conveyance shutter 615 is in a form of a generally hollow cylindrical member, and is disposed over the horizontal conveyance case 612. The waste toner conveyance shutter 615 is formed with a communication opening 615*a*, and is angularly rotatable relative to the horizontal conveyance case 612.

The waste toner conveyance shutter 615 is movable between an open position and a closed position by pivotal movement of the waste toner conveyance shutter 615 relative to the horizontal conveyance case 612. In the open position, the waste toner outlet opening 612*a* and the communication opening 615*a* are communicated with each other opening the waste toner outlet opening 612*a*. In the closed position, the waste toner outlet opening 612*a* is out of communication with the communication opening 615*a* closing the waste toner outlet opening 612*a*.

An urging member such as a spring 618 (FIG. 9) is connected to the waste toner conveyance shutter 615 to urge the waste toner conveyance shutter 615 toward the closed position. The first abutment segment 616 is provided at the waste toner conveyance shutter 615 and is movable integrally with the waste toner conveyance shutter 615. The first abutment segment 616 is abuttable on the waste toner retaining portion 527 of the toner cartridge 52.

In the waste toner conveying unit 61, the first abutment segment 616 is out of abutment with the toner cartridge 52 when the toner cartridge 52 attached to the process cartridge 51 is at the second position. Hence, the waste toner conveyance shutter 615 is at the closed position by the urging force of the spring 618. On the other hand, the first abutment segment 616 is in abutment with the toner cartridge 52 when the toner cartridge 52 attached to the process cartridge 51 is at the first position. Hence, the waste toner conveyance shutter 615 is moved to the open position against the urging force of the spring 618.

The second abutment segment 617 is provided also at the waste toner conveyance shutter 615, and is movable integrally with the waste toner conveyance shutter 615. The second abutment segment 617 is abuttable on the inlet opening shutter 528 of the toner cartridge 52.

(Leg Portion)

The toner cartridge 52 includes a leg 163 movable between an accommodated position indicated by two dotted chain line in FIGS. 8A and 8B and a protruding position indicated by solid line in FIGS. 8A and 8B. In the accommodated position, the leg 162 is accommodated inward of the frame 511 of the process cartridge 51. In the protruding position, the leg 163 protrudes outward of the frame 511. The leg 163 is urged to the protruding position by an urging member (not illustrated).

The leg 163 is configured to be moved to the accommodated position against the urging force of the urging member when the process cartridge 51 is attached to the housing 2. The leg 163 is configured to be moved to the protruding position by the urging force of the urging member when the process cartridge 51 is detached from the housing 2.

[Opening/Closing Operation of Shutter]

Figure 11:
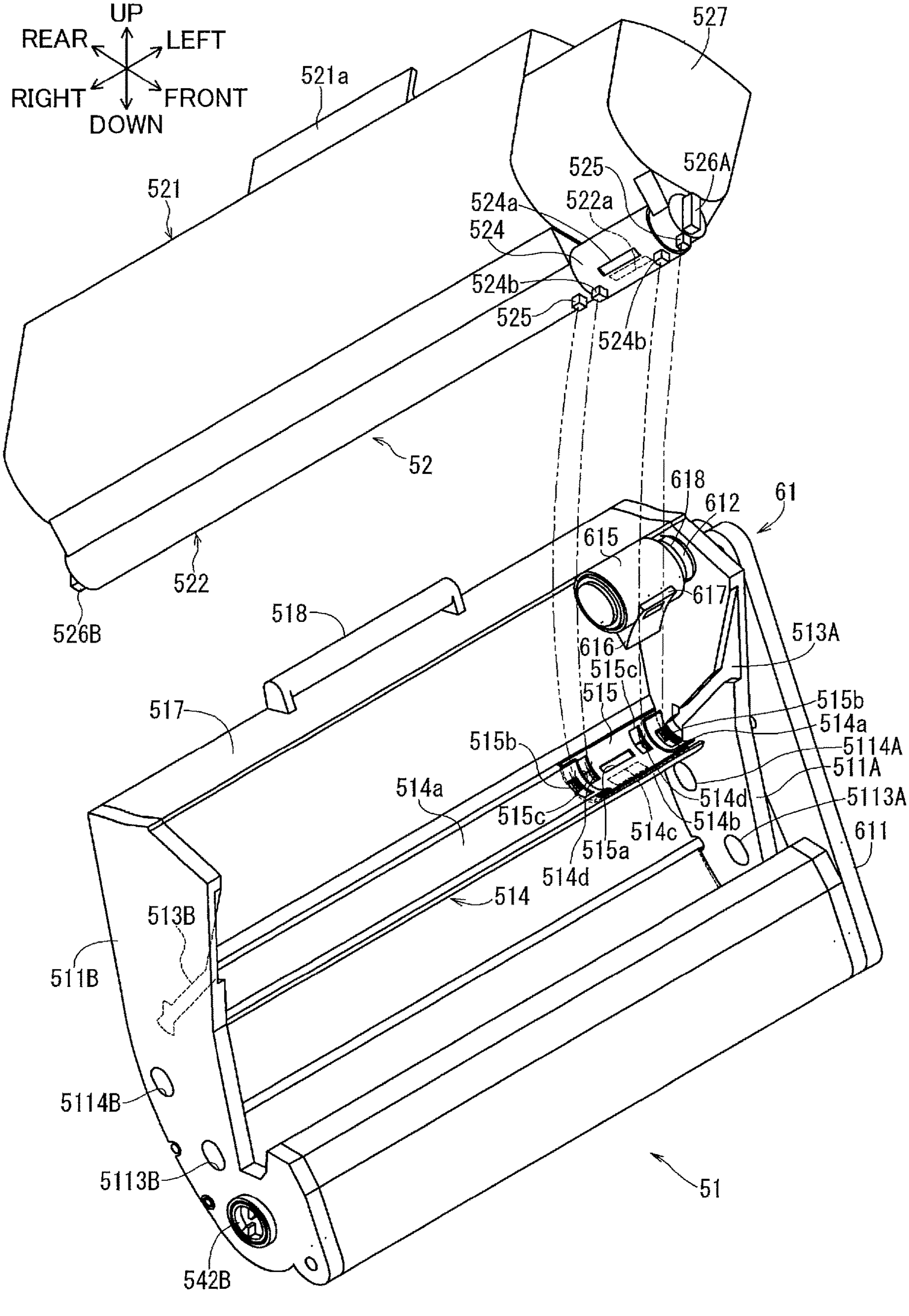
FIG. 11 is a perspective view illustrating a process of attachment of the toner cartridge to the process cartridge, and particularly illustrating engagement of a first protruding portion and a second protruding portion with a first recessed portion and a second recessed portion, respectively.

As illustrated in FIG. 11, the toner cartridge shutter 524 is at the closed position and the process cartridge shutter 515 is closed, in a detached state of the toner cartridge 52 from the process cartridge 51. Further, the inlet opening shutter 528 is at the closed position, and the waste toner conveyance shutter 615 is at the closed position.

Then, from this state, when the guide ribs 526A, 526B of the toner cartridge 52 are inserted into the guide grooves 513A, 513B of the first and second side frames 511A, 511B, the toner cartridge 52 is guided with its inclined posture and the guide ribs 526A, 526B reach the lower end portions of the guide grooves 513A, 513B. Thus, the toner cartridge 52 is attached to the process cartridge 51.

At this time, the first protruding portions 524*b* of the toner cartridge shutter 524 is engaged with the first recessed portions 514*d* of the opening/closing surface portion 514*b* of the connection frame 514 of the process cartridge 51, and at the same time, the second protruding portions 525 of the toner cartridge 52 is engaged with the second recessed portions 515*b* of the process cartridge shutter 515.

Figure 12B:
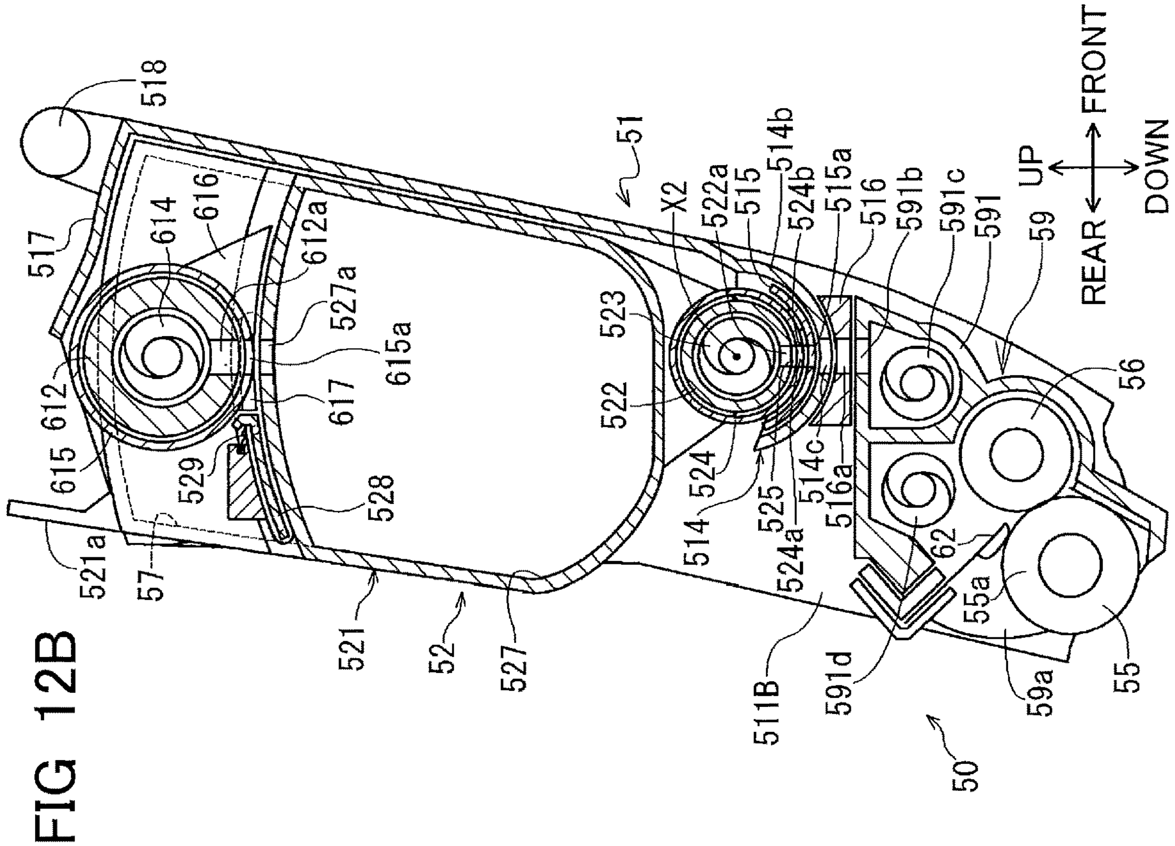
FIG. 12B is a cross-sectional side view of the process cartridge and the toner cartridge attached thereto and positioned at a second position.
Figure 12A:
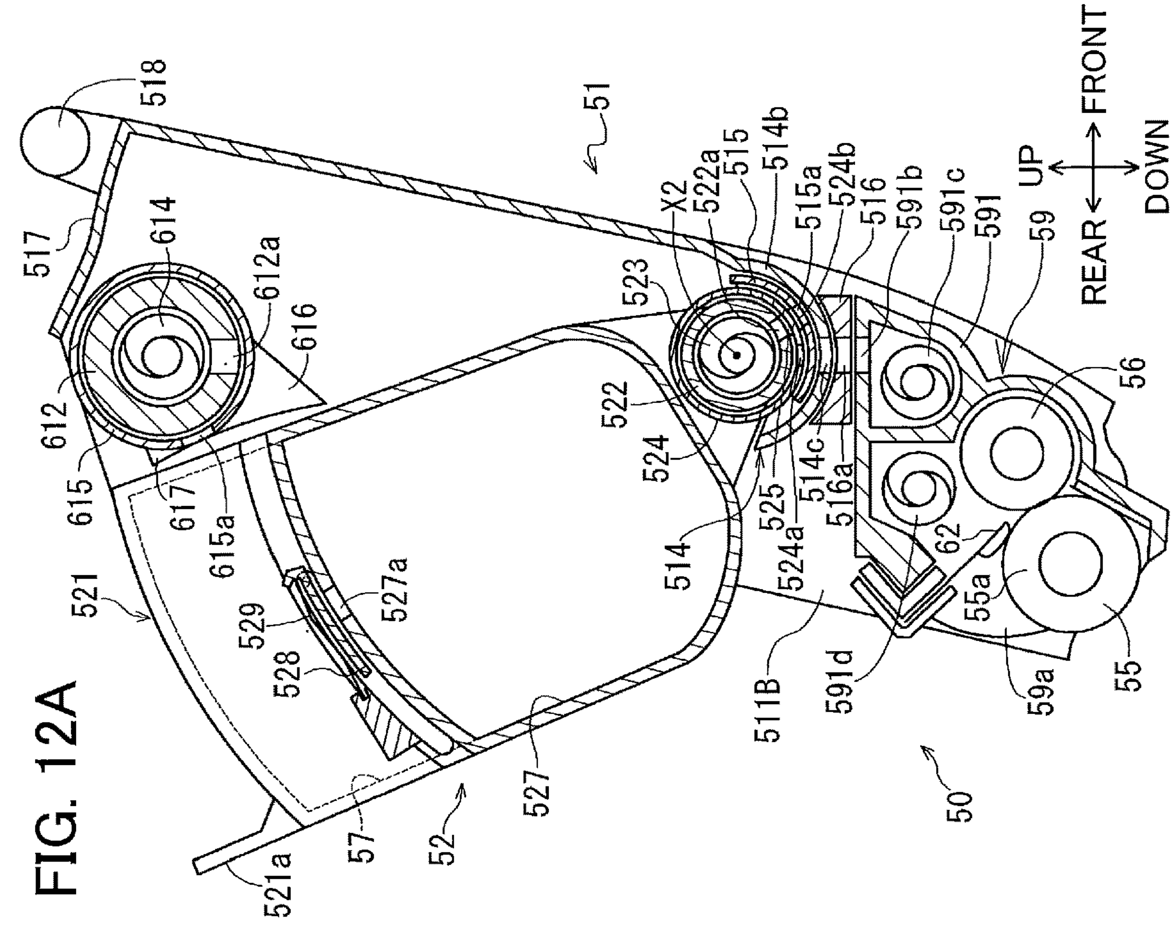
FIG. 12A is a cross-sectional side view of the process cartridge and the toner cartridge attached thereto and positioned at a first position.

Further, as illustrated in FIG. 12A, the toner cartridge 52 is at the second position when the toner cartridge 52 is attached to the process cartridge 51 by inserting the guide ribs 526A, 526B in the guide grooves 513A, 513B.

The toner cartridge 52 reaching the lower end portions of the guide grooves 513A, 513B (that is, the locking grooves 5131A, 5131B) is pivotally movable about the pivot axis X2 of the connecting portion 522. Hence, as illustrated in FIG. 12B, the toner cartridge 52 that is positioned at the second position is moved to the first position by pivotally moving the toner cartridge 52 frontward.

In the process unit 50, the toner cartridge shutter 524 and the process cartridge shutter 515 can be opened and closed by pivotally moving the toner cartridge 52 attached to the process cartridge 51 between the second position and the first position.

As illustrated in FIG. 12A, in a state where the toner cartridge 52 attached to the process cartridge 51 is at the second position, the toner supply opening 522*a* of the toner cartridge casing 521 is positioned frontward of the communication opening 524*a* of the toner cartridge shutter 524. Hence the toner cartridge shutter 524 is at the closed position closing the toner supply opening 522*a*. Further, the communication opening 515*a* of the process cartridge shutter 515 is positioned frontward of the toner inlet opening 514*c* of the cartridge frame 511. Hence, the process cartridge shutter 515 is at the closed position closing the toner inlet opening 514*c*.

Then, in accordance with pivotal movement of the toner cartridge 52 relative to the process cartridge 51 to the second position as illustrated in FIG. 12B, the toner cartridge 52 and the toner cartridge shutter 524 are relatively moved in the circumferential direction, so that the toner cartridge shutter 524 is moved to the open position opening the toner supply opening 522*a*, and at the same time, the process cartridge 51 and the process cartridge shutter 515 are relatively moved in the circumferential direction to move the process cartridge shutter 515 to the open position opening the toner inlet opening 514*c*.

Specifically, as a result pivotal movement of the toner cartridge 52 from the second position to the first position, the toner supply opening 522*a* of the toner cartridge casing 521 is moved rearward. On the other hand, the toner cartridge shutter 524 is immovable in the circumferential direction because of engagement between the first protruding portions 524*b* of the toner cartridge shutter 524 and the first recessed portions 514*d* of the connection frame 514 of the process cartridge 51.

Accordingly, the toner supply opening 522*a* of the toner cartridge casing 521 and the communication opening 524*a* of the toner cartridge shutter 524 are relatively moved in the circumferential direction to bring the toner supply opening 522*a* into linear alignment with the communication opening 524*a* in upward/downward direction. Thus, the toner supply opening 522*a* and the communication opening 524*a* are communicated with each other opening the toner cartridge shutter 524. That is, the toner cartridge shutter 524 is moved to the open position to open the toner supply opening 522*a*.

Further, in accordance with pivotal movement of the toner cartridge 52 from the second position to the first position, the second protruding portions 525 of the toner cartridge casing 521 is moved rearward. The process cartridge shutter 515 is also moved rearward along with the second protruding portions 525 because of the engagement of the second protruding portions 525 with the second recessed portions 515*b* of the process cartridge shutter 515. On the other hand, the opening/closing surface portion 514*b* of the connection frame 514 of the process cartridge 51 is immovable.

Therefore, the communication opening 515*a* of the process cartridge shutter 515 and the toner inlet opening 514*c* of the opening/closing surface portion 514*b* are relatively moved in the circumferential direction to bring the communication opening 515*a* into linear alignment with the toner inlet opening 514*c* in upward/downward direction. Hence, the communication opening 515*a* and the insertion hole 515*c* are communicated with each other opening the process cartridge shutter 515. In other words, the process cartridge shutter 515 is moved to the open position opening the toner inlet opening 514*c*.

Reversely, in accordance with pivotal movement of the toner cartridge 52 from the first position to the second position, the toner cartridge 52 and the toner cartridge shutter 524 are relatively moved in circumferential direction closing the toner cartridge shutter 524.

That is, the toner cartridge shutter 524 is moved to the closed position to close the toner supply opening 522*a*. Further, the process cartridge 51 and the process cartridge shutter 515 are relatively moved in the circumferential direction to close the process cartridge shutter 515.

As illustrated in FIG. 12A, in a state where the toner cartridge 52 attached to the process cartridge 51 is at the second position, the inlet opening shutter 528 is moved to the closing position for closing the inlet opening 527*a* by the urging force of the spring 529. Further, the first abutment segment 616 does not abut on the toner cartridge 52 so that the waste toner conveyance shutter 615 is at the closing position for closing the waste toner outlet opening 612*a*.

As illustrated in FIG. 12B, by pivotally moving the toner cartridge 52 relative to the process cartridge 51 from the second position to the first position, the second abutment segment 617 is brought into abutment with the inlet opening shutter 528 to move the inlet opening shutter 528 to the opening position for opening the inlet opening 527*a* against the urging force of the spring 529. Hence, the inlet opening 527*a* is opened.

Further, the first abutment segment 616 is brought into abutment with the toner cartridge 52 to move the waste toner conveyance shutter 615 to the opening position for opening the waste toner outlet opening 612*a* against the urging force of the urging member. Hence, the waste toner outlet opening 612*a* is opened to communicate with the inlet opening 527*a*. Thus, the waste toner conveyed to the waste toner outlet opening 612*a* can be discharged into the waste toner retaining portion 527 through the waste toner outlet opening 612*a* and the inlet opening 527*a*.

Reversely, by pivotally moving the toner cartridge 52 relative to the process cartridge 51 from the first position to the second position, the second abutment segment 617 is separated from the inlet opening shutter 528 to move the inlet opening shutter 528 to the closing position for closing the inlet opening 527*a* by the urging force of the spring 529. Hence, the inlet opening 527*a* is closed. Further, the first abutment segment 616 is separated the toner cartridge 52 to move the waste toner conveyance shutter 615 to the closing position for closing the waste toner outlet opening 612*a* by the urging force of the urging member. Hence, the waste toner outlet opening 612*a* is closed.

As such, the image forming apparatus 1 is configured such that, when the toner cartridge 52 is at the first position, the toner cartridge shutter 524 is at the open position for opening the toner supply-opening 522*a*, the process cartridge shutter 515 is at the open position for opening the toner inlet opening 514*c*, and when the toner cartridge 52 is at the second position, the toner cartridge shutter 524 is at the closed position for closing the toner supply-opening 522*a*, the process cartridge shutter 515 is at the closed position for closing the toner inlet opening 514*c*.

With this structure, in a state where the toner cartridge 52 is at the second position allowing the toner cartridge 52 to be detachable from the process cartridge 51, both the toner supply opening 522*a* and the toner inlet opening 514*c* are closed by the toner cartridge shutter 524 and the process cartridge shutter 515, respectively. Hence, leakage of toner through the toner supply opening 522*a* and the toner inlet opening 514*c can be restrained.*

Further, if large amount of toner exists at a position adjacent to the toner supply opening 522*a* at the time of closure of the toner cartridge shutter 524, leakage of toner through the toner inlet opening 514*c* may occur during closing operation of the toner cartridge shutter 524.

However, such toner leakage is avoidable. That is, the process cartridge 51 to which the toner cartridge 52 is attached is detached from the housing 2. Then, the process cartridge 51 is laid on a horizontal plane with such a posture that the process cartridge handle 518 is positioned frontward and the photosensitive drum 54 is positioned rearward or vice/versa. Then, the toner cartridge 52 is detached from the process cartridge 51. Because of the horizontal posture of the process cartridge 51 laid on the horizontal plane, toner stagnated adjacent to the toner supply opening 522*a* can be moved to a region away from the toner supply opening 522*a* because of gravity. Hence, clinging of toner to the toner cartridge shutter 524 moving toward the closed position is unlikely to occur.

[Detachment of Process Cartridge and Toner Cartridge]

As illustrated in FIG. 1, the four process units 50 of the image forming unit 5 includes a first process unit 50-1 which is a frontmost process unit 50, a second process unit 50-2 positioned immediately rearward of the first process unit 50-1, a third process unit 50-3 positioned immediately rearward of the second process unit 50-2, and a fourth process unit 50-4 positioned immediately rearward of the third process unit 50-3 and that is a rearmost process unit 50.

The first process unit 50-1 includes a first process cartridge 51-1 and a first toner cartridge 52-1. The second process unit 50-2, includes a second process cartridge 51-2 and a second toner cartridge 52-2. The third process unit 50-3 includes a third process cartridge 51-3 and a third toner cartridge 52-3. The fourth process unit 50-4 includes a fourth process cartridge 51-4 and a fourth toner cartridge 52-4.

The first process cartridge 51-1 includes a first photosensitive drum 54-1, the second process cartridge 51-2 includes a second photosensitive drum 54-2, the third process cartridge 51-3 includes a third photosensitive drum 54-3, and the fourth process cartridge 51-4 includes a fourth photosensitive drum 54-4.

The developing roller 55 of the first process cartridge 51-1 is an example of a first developing roller, and the developing roller 55 of the second process cartridge 51-2 is an example of a second developing roller. The second process cartridge 51-2 is attachable to and detachable from the housing 2, and is positioned adjacent to the first process cartridge 51-1 attached to the housing 2. Multiple color printing can be performed by the second process cartridge 51-2, the third process cartridge 51-3 and the fourth process cartridge 51-4 in addition to the first process cartridge 51-1.

The second process cartridge 51-2, the third process cartridge 51-3 and the fourth process cartridge 51-4 those attached to the housing 2 are juxtaposed to the first process cartridge 51-1 in frontward/rearward direction. Further, the rotation axes X1 of the second photosensitive drum 54-2, the third photosensitive drum 54-3 and the fourth photosensitive drum 54-4 extend parallel to the rotation axis X1 of the first photosensitive drum 54-1 in the attached state of the process cartridges 51-1 through 51-4 to the housing 2.

The process cartridge handle 518 is positioned on the upper end portion of the process cartridge 51, and the toner cartridge handle 521*a* is positioned on the upper end portion of the toner cartridge 52. The process cartridge handle 518 is positioned frontward of the toner cartridge handle 521*a*. That is, the process cartridge handle 518 is positioned closer to the front wall 21 of the housing 2 than the toner cartridge handle 521*a* is to the front wall 21.

In the image forming apparatus 1, the process cartridge 51 can be detached from the housing 2 while the top cover 2 is opened. The front end portion of the top cover 23 is a free end portion positioned at near side for a user. Further, as described above, the sheet supply tray 10 is pulled out frontward to the separated position, which is also near side for the user.

In the open state of the top cover 23, the process cartridge handle 518 is positioned closer to the user than the toner cartridge handle 521*a* is to the user. Hence, the process cartridge handle 518 rather than the toner cartridge handle 521*a* is accessible to the user. Thus, the process cartridge 51 to which the toner cartridge 52 is attached can be detached from the housing 2 by user's gripping the process cartridge handle 518. Consequently, the user can easily and properly select the process cartridge 51 rather than toner cartridge 52 for the detachment from the housing 2.

In the image forming apparatus 1, in the state where the process cartridge 51 is attached to the housing 2 and the toner cartridge 52 is attached to the process cartridge 51, the toner cartridge 52 is positioned above the developing frame 591 such that the toner supply opening 522*a* of the toner cartridge 52 and the toner inlet opening 514*c* of the process cartridge 51 face with each other in upward/downward direction.

In the state where the process cartridge 51 to which the toner cartridge 52 is attached is attached to the housing 2, the toner cartridge 52 cannot be detached from the process cartridge 51.

Figure 13:
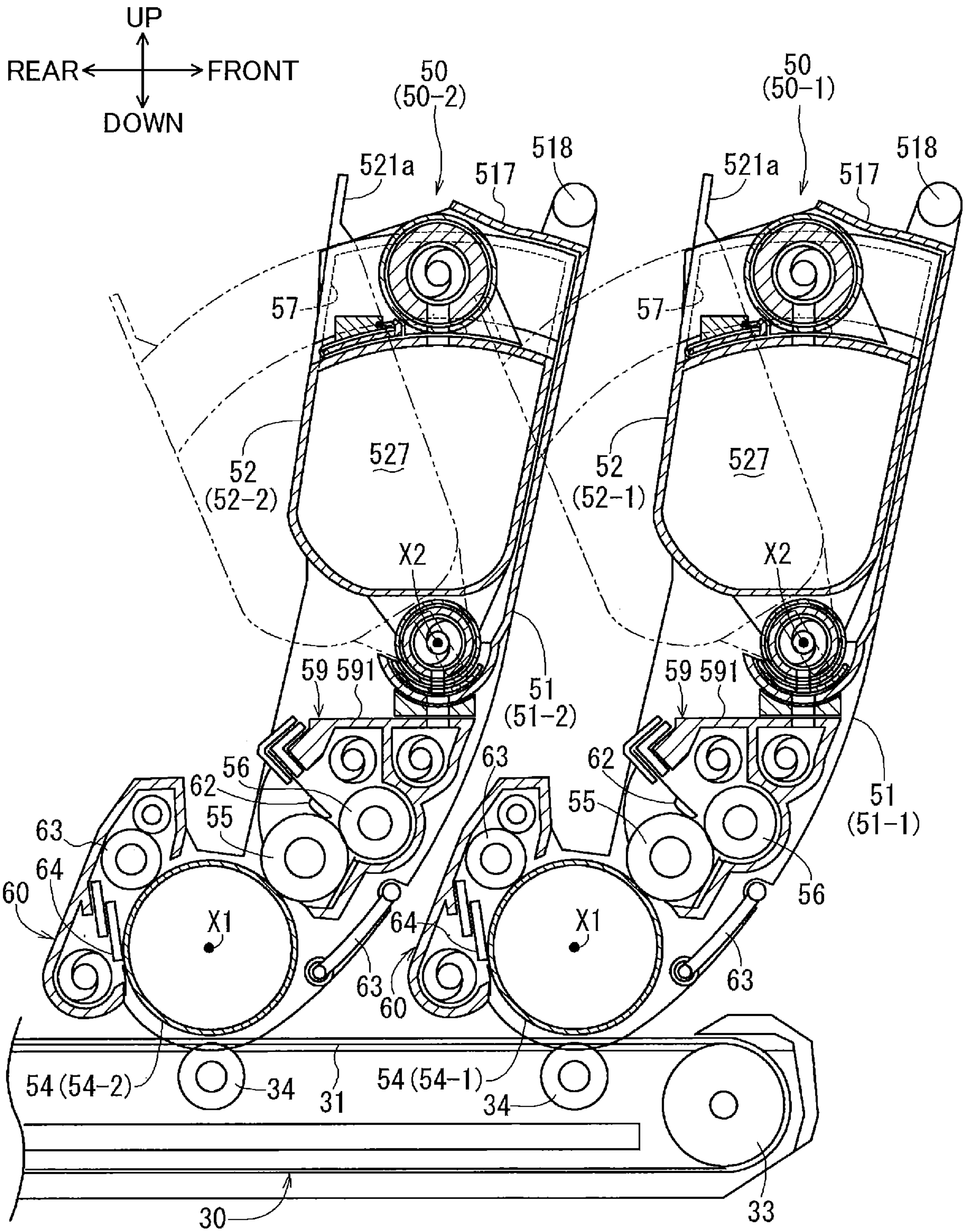
FIG. 13 is a cross-sectional side view illustrating a state where a first process cartridge carrying a first toner cartridge and a second process cartridge carrying a second toner cartridge are attached to a housing of the image forming apparatus.

For example, as illustrated in FIG. 13, in a state where the first process cartridge 51-1 to which the first toner cartridge 52-1 is attached is attached to the housing 2 and the second process cartridge 51-2 to which the second toner cartridge 52-2 is attached is attached to the housing 2, if the first toner cartridge 52-1 is pivotally moved from the first position toward the second position, the first toner cartridge 52-1 abuts against the second toner cartridge 52-2 during its pivotal movement toward the second position, so that the second toner cartridge 52-2 cannot reach the second position.

This mechanical interference can prevent the first toner cartridge 52-1 alone from being detached from the first process cartridge 51-1. In other words, detachment of the first toner cartridge 52-1 from the first process cartridge 51-1 can be prevented with such a simple structure.

Particularly, according to the first embodiment, in the state where the first process cartridge 51-1 to which the first toner cartridge 52-1 is attached is attached to the housing 2, the second process cartridge 51-2 adjacent to the first process cartridge 51-1 can prevent the first toner cartridge 52-1 alone from being detached from the first process cartridge 51-1.

On the other hand, in state where the first process cartridge 51-1 to which the first toner cartridge 52-1 is attached is detached from the housing 2, no mechanical interference of the first toner cartridge 52-1 with the second process cartridge 51-2 occur, permitting the second toner cartridge 52-1 to be pivotally moved from the first position to the second position. Hence, the first toner cartridge 52-1 can be detached from the first process cartridge 51-1. In this way, the toner cartridge 52 can be detachable from the process cartridge 51 in the detached state of the process cartridge 51 from the housing 2.

For the exchange of the toner cartridge 52 for a new toner cartridge 52 in the image forming apparatus 1 where the process cartridge 51 to which the toner cartridge 52 is attached is attached to the housing 2, the user may be distressed by the alternative, that is, whether only the toner cartridge 52 should be accessible to the user for detaching only the toner cartridge 52, or whether the process cartridge 51 should be accessible to the user for detaching both the process cartridge 51 and the toner cartridge 52.

Further, in a structure where the toner cartridge 52 is positioned above the developing frame 591, a mechanism for supplying toner from the toner cartridge 52 to the developing frame 591 can be simplified, since the gravity can be utilized for the toner supply. However, if the toner cartridge 52 is detached from the process cartridge 51 while the toner cartridge 52 is positioned above the developing frame 591, toner leakage may occur since the toner supply opening 522*a* faces downward.

Against these problems, in the image forming apparatus 1 according to the first embodiment, in the state where the process cartridge 51 to which the toner cartridge 52 is attached is attached to the housing 2, the toner cartridge 52 cannot be solely detached from the housing 2. In order to detach the toner cartridge 52 from the process cartridge 51, two detaching procedure is necessary, that is, the process cartridge 51 to which the toner cartridge 52 is attached is detached from the housing 2, and then, the toner cartridge 52 is detached from the process cartridge 51. Hence, improper detaching operation is unlikely to occur without user's confusion to the detaching operation.

Figure 14A:
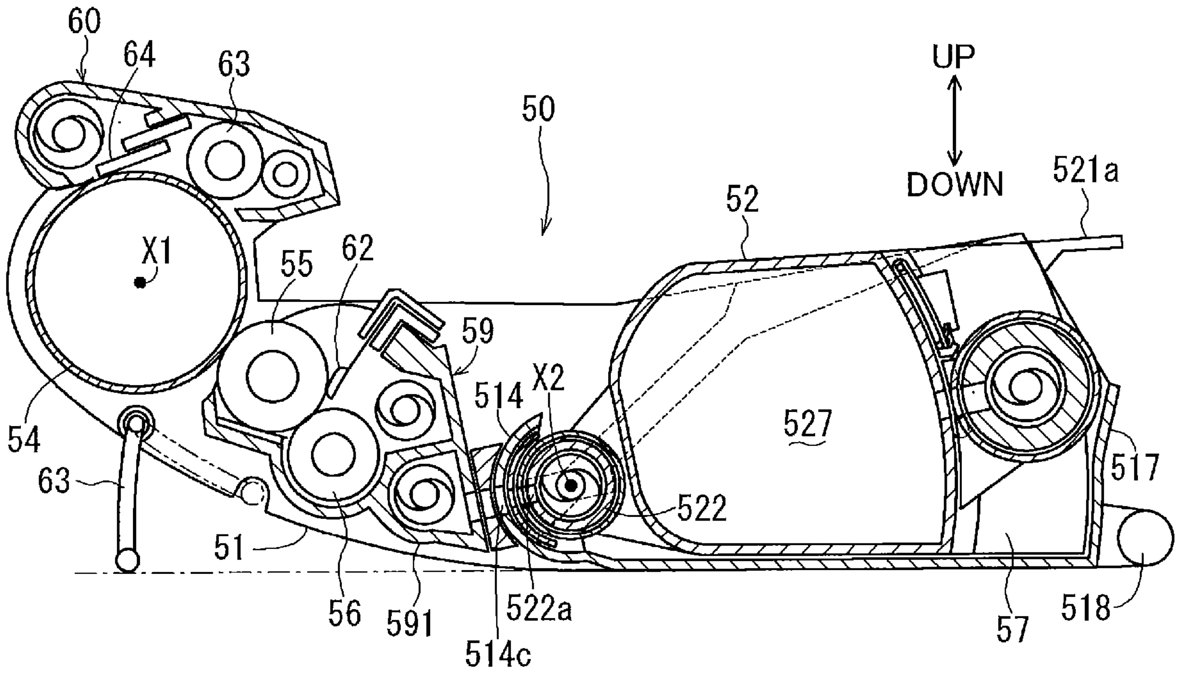
FIG. 14A is a cross-sectional view of the process cartridge detached from the housing and laid on a horizontal plane to have a horizontal posture, and particularly illustrates the first position of the toner cartridge.

Further, for detaching the toner cartridge 52 from the process cartridge 51, as illustrated in FIG. 14A, the process cartridge 51 is detached along with the toner cartridge 52 from the housing 2, and then, the vertical posture of the process cartridge 51 at the attached state of the process cartridge 51 to the housing 2 is changed to the horizontal posture by laying the process cartridge 51 on the horizontal plane. At this time, the leg 63 of the process cartridge 51 is moved to the protruding position, so that a tip end portion of the leg 63 is seated on the horizontal plane for supporting the process cartridge 51 with the horizontal posture. The leg 63 can stabilize the horizontal posture of the process cartridge 51.

Figure 14B:
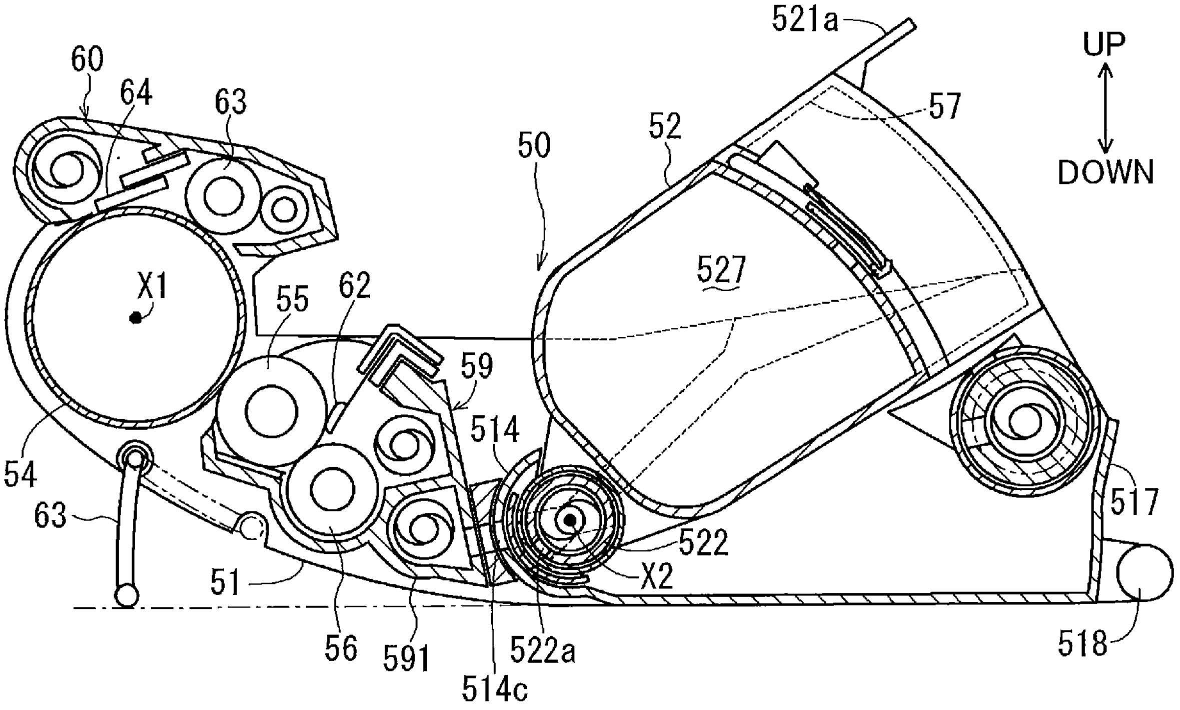
FIG. 14B is a cross-sectional view of the process cartridge detached from the housing and laid on the horizontal plane to have the horizontal posture, and particularly illustrates the second position of the toner cartridge.
Figure 15:
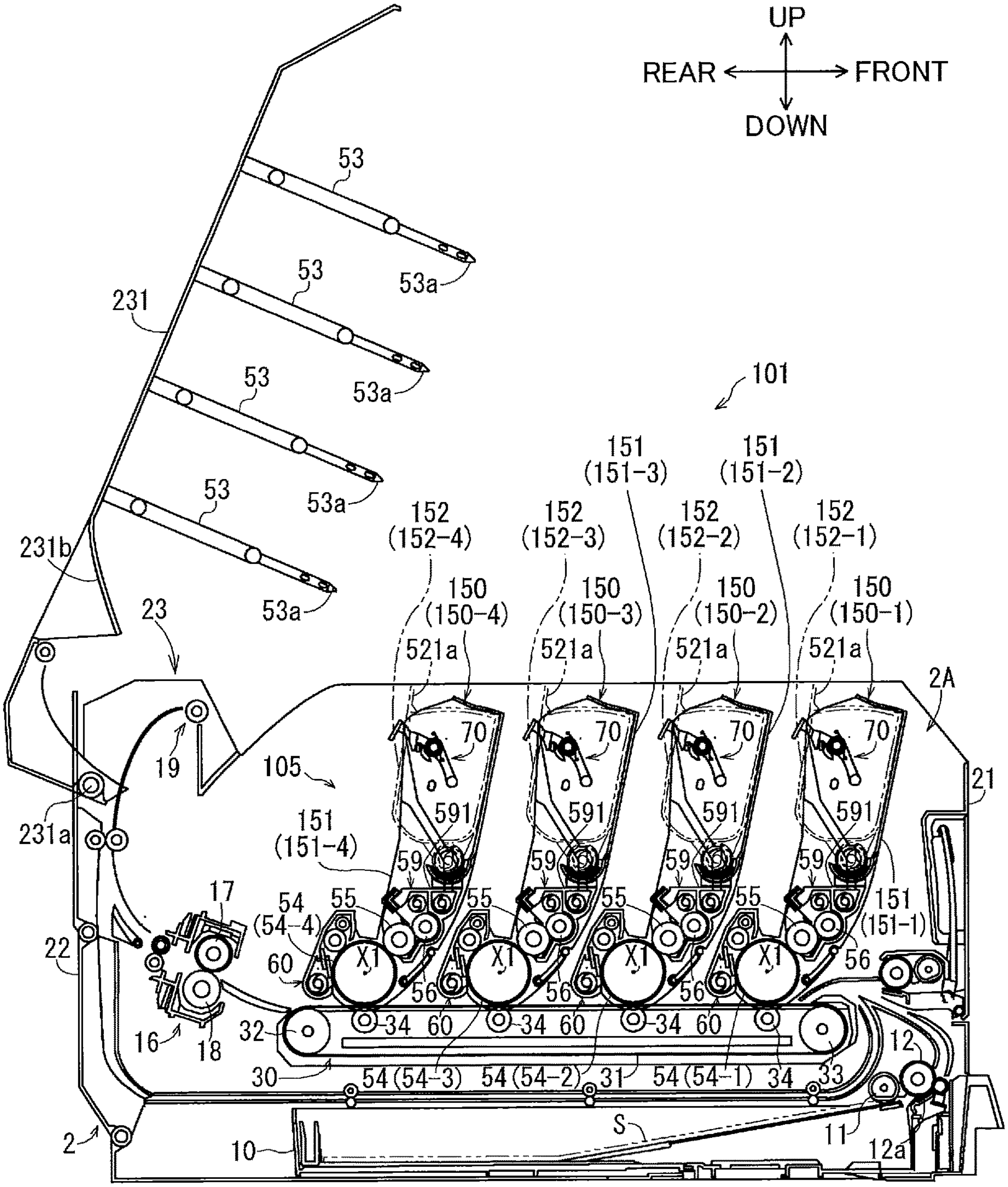
FIG. 15 is a cross-sectional side view of an image forming apparatus according to a second embodiment in which a process cartridge is provided with a lock lever.

From the state illustrated in FIG. 14A, in accordance with the pivotal movement of the toner cartridge 52 from the first position to the second position for detaching the toner cartridge 52 from the process cartridge 51 as illustrated in FIG. 14B, the toner supply opening 522*a* can be moved away from the toner inlet opening 514*c* after the confronting direction between the toner supply opening 522*a* and the toner inlet opening 514*c* is changed to the horizontal direction (FIG. 14A) from the vertical direction (FIG. 13). Hence, toner accumulated by its gravity around the toner supply opening 522*a* due to vertical posture of the process cartridge 51 (FIG. 13) can be moved away from the toner supply opening 522*a* because of change in posture of the process cartridge 51 (FIGS. 14A, 14B). Accordingly, a danger of leakage of toner through the toner supply opening 522*a* during detaching operation can be largely reduced.

Further, as illustrated in FIG. 13, in the state where the process cartridge 51 is attached to the housing 2 and the toner cartridge 52 is attached to the process cartridge 51, the first connection frame 517 of the process cartridge 51 is positioned opposite to the photosensitive drum 54 with respect to the toner cartridge 52 in upward/downward direction.

With this structure, in the state where the process cartridge 51 to which the toner cartridge 52 is attached is attached to the housing 2, the toner cartridge 52 can be less likely to be detached from the process cartridge 51. Further, the structure according to the first embodiment can allow the user to facilitate visual recognition that the toner cartridge 52 cannot be solely detached from the process cartridge 51 when the toner cartridge 52 is at the first position, and allows the user to recognize necessity of pivotally moving the toner cartridge 52 for detaching the toner cartridge 52 from the process cartridge 51.

Further, the image forming apparatus 1 provides the structure such that the toner cartridge 52 faces the first connection frame 517 when the toner cartridge 52 is at the first position, and the toner cartridge 52 is offset from the first connection frame 517 when the toner cartridge 52 is at the second position.

This structure can allow the user to visually recognize that detachment of the toner cartridge 52 from the process cartridge 51 is difficult when the toner cartridge 52 is at the first position, and to visually recognize the necessity of pivotally moving the toner cartridge 52 to the second position to detach the toner cartridge 52 from the process cartridge 51.

[Regulating Member]

An image forming apparatus 101 according to a second embodiment will be described with reference to FIGS. 15 through 23, wherein like parts and components are designated by the same reference numerals as those shown in FIGS. 1 through 14B. The image forming apparatus 101 according to the second embodiment is the same as the image forming apparatus 1 according to the first embodiment except an image forming unit 105 including a process unit 150. The process unit 150 includes a process cartridge 151 and a toner cartridge 152.

According to the second embodiment, the process cartridge 151 further includes a lock lever 70, which is an example of a regulation member. The lock lever 70 is movable between a regulating position where the lock lever 70 prevents the toner cartridge 152 from moving from the first position to the second position and a non-regulating position where the lock lever 70 permits the toner cartridge 152 to move from the first position to the second position.

Figure 20:
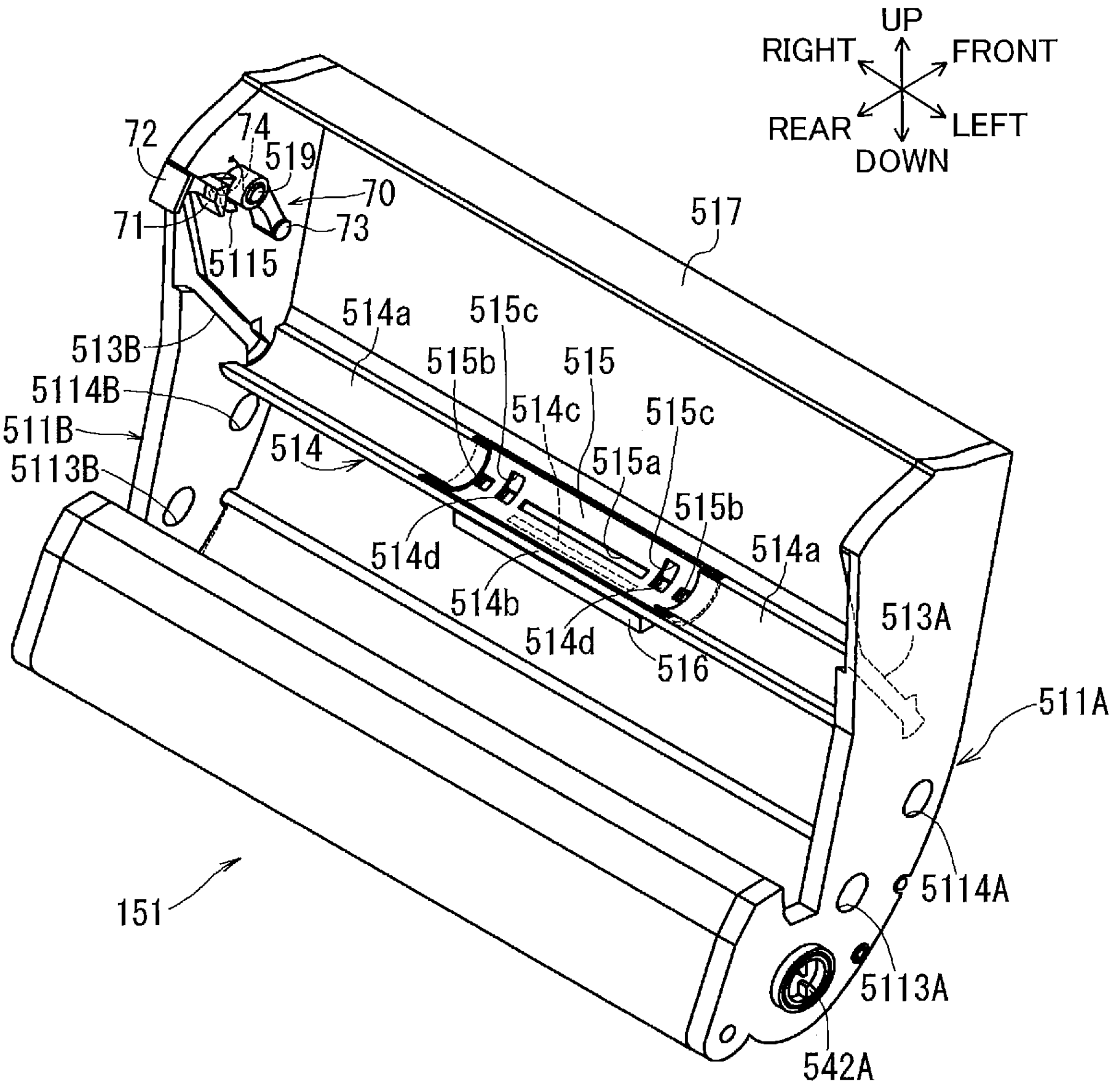
FIG. 20 is a perspective view of the process cartridge provided with the lock lever in the image forming apparatus according to the second embodiment.
Figure 21:
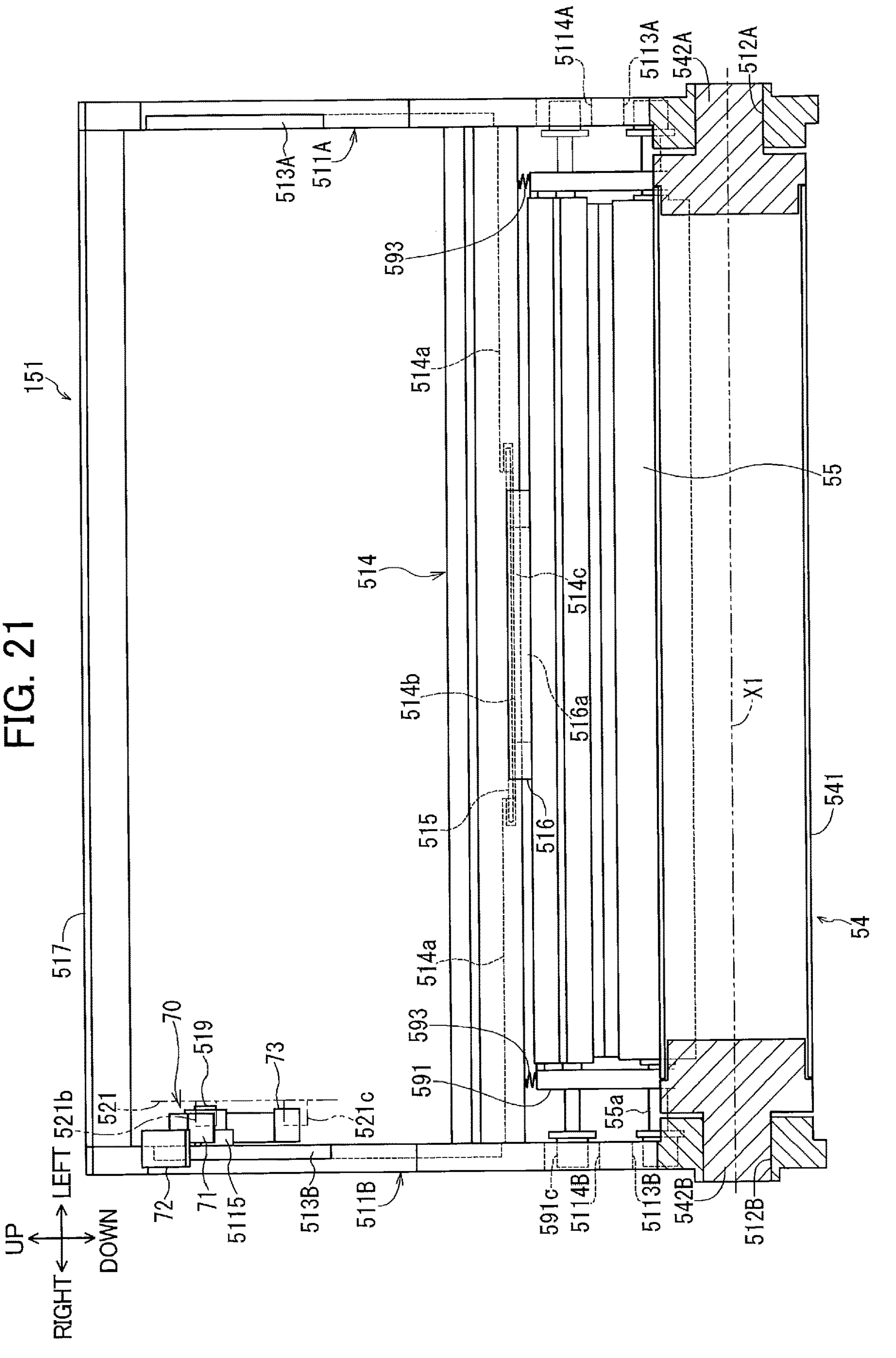
FIG. 21 is a cross-sectional rear view of the process cartridge provided with the lock lever in the image forming apparatus according to the second embodiment.
Figure 22:
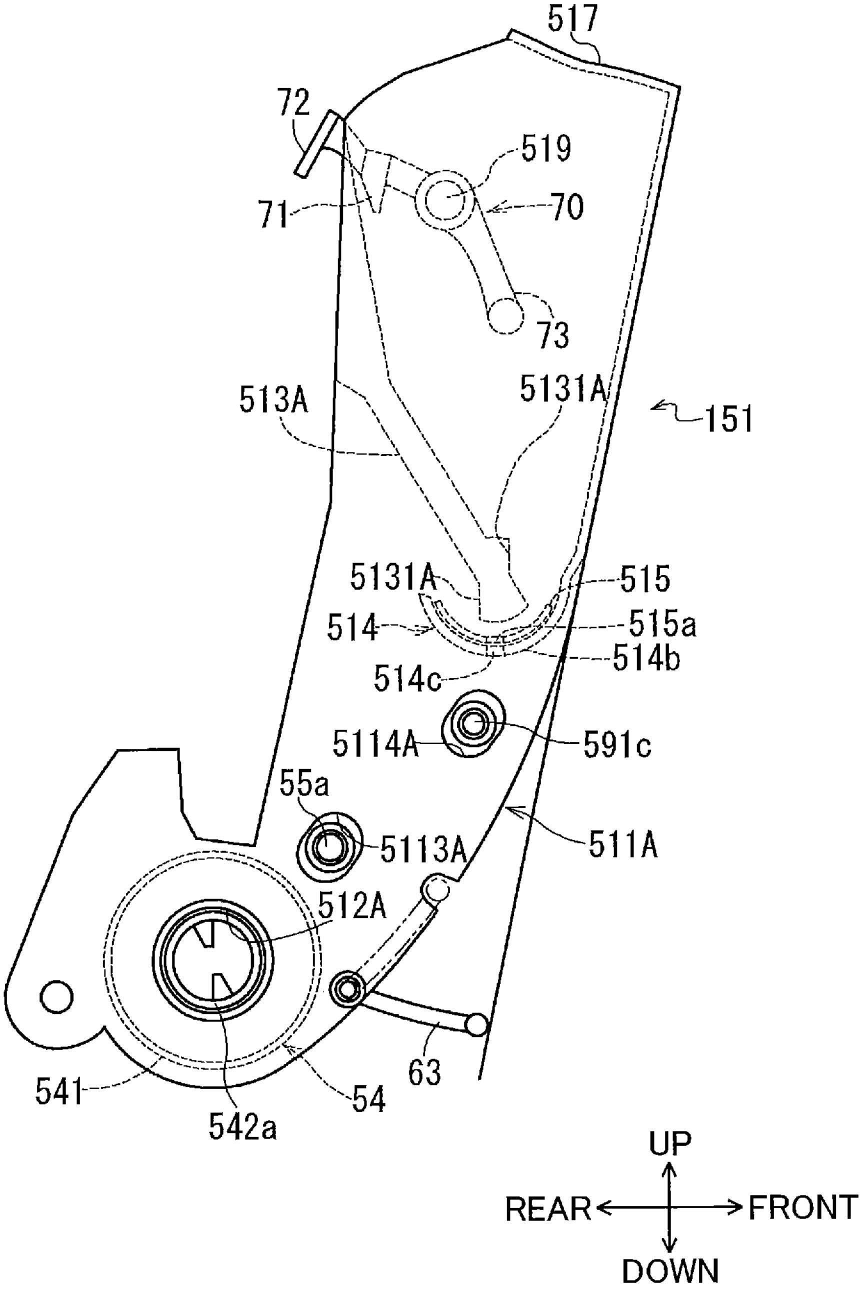
FIG. 22 is a side view of the process cartridge provided with the lock lever in the image forming apparatus according to the second embodiment.

As illustrated in FIGS. 16, and 20 through 22, the lock lever 70 is pivotally movably supported by the second side frame 511B of the process cartridge 151. A pivot shaft 519 extends inward from the second side frame 511B in leftward/rightward direction (FIG. 21). The lock lever 70 is pivotally movably supported by the pivot shaft 519. The lock lever 70 includes a locking pawl 71, an operation lever 72, and a pressure lever 73. The locking pawl 71, the operation lever 72, and the pressure lever 73 are integrally pivotally movable about an axis of the pivot shaft 519. The process cartridge 151 further includes a spring 74 urging the lock lever 70 in the pivotally moving direction.

Figure 16:
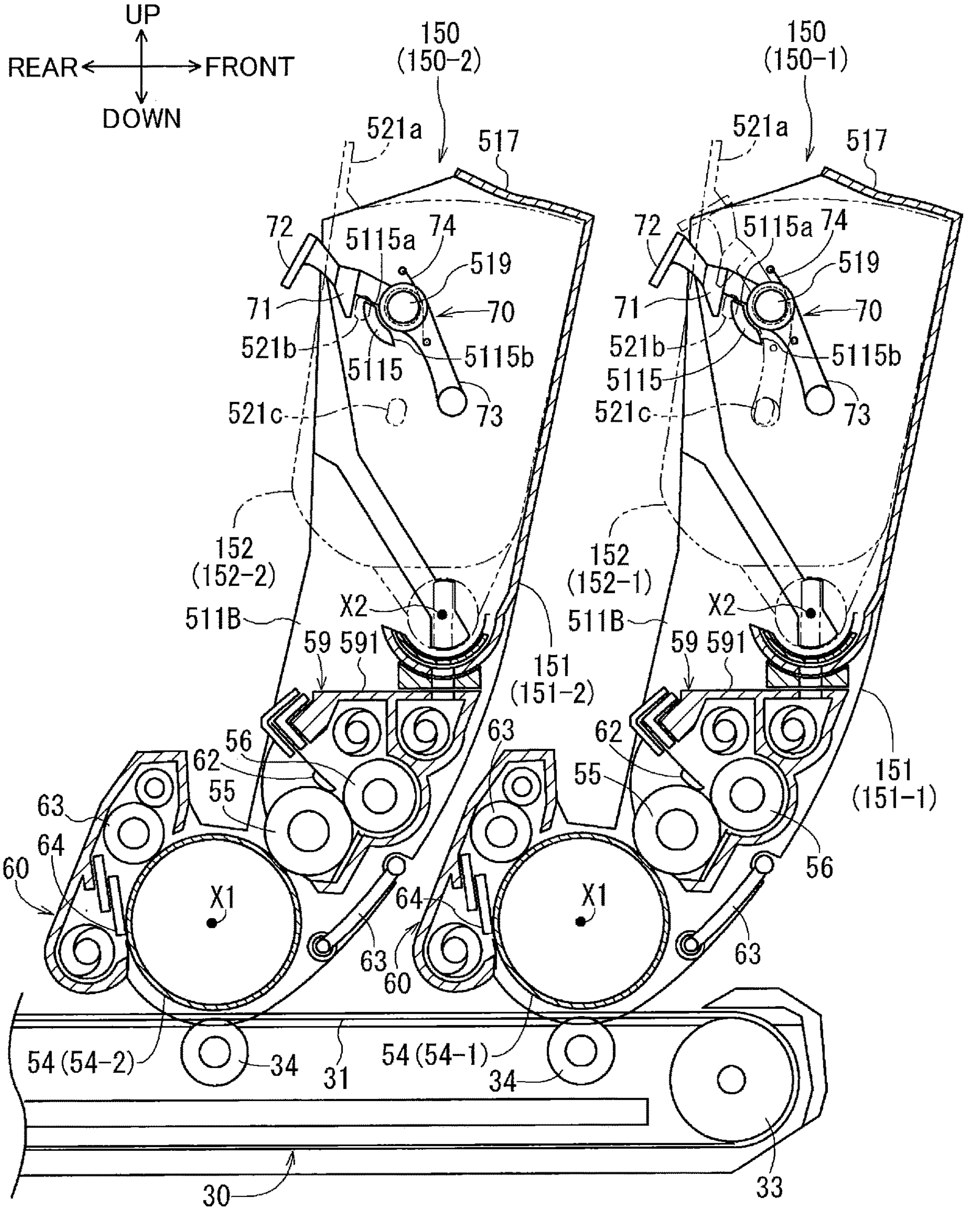
FIG. 16 is a cross-sectional side view illustrating a state where a first process cartridge having the lock lever and a second process cartridge having the lock lever are attached to a housing of the image forming apparatus according to the second embodiment.

As illustrated in FIGS. 16 and 19, the toner cartridge 152 includes a first protrusion 521*b* engageable with the locking pawl 71, and a second protrusion 521*c* configured to abut against the pressure lever 73. The first protrusion 521*b* and the second protrusion 521*c* protrude outward in leftward/rightward direction from the right surface of the toner cartridge casing 521.

The lock lever 70 is pivotally movable about the axis of the pivot shaft 519 between a regulating position as indicated by a solid line in FIG. 16 and a non-regulating position as indicated by a two dotted chain line in FIG. 16. The spring 74 urges the lock lever 70 toward the regulating position.

When the lock lever 70 is at the regulating position, the locking pawl 71 is engaged with the first protrusion 521*b* preventing the toner cartridge 152 from moving from the first position to the second position. On the other hand, when the lock lever 70 is at the non-regulating position, engagement between the locking pawl 71 and the first protrusion 521*b* is released, permitting the toner cartridge 152 to move from the first position to the second position.

The operation lever 72 is configured to manually switch the position of the lock lever 70 between the regulating position and the non-regulating position. The lock lever 70 is maintained at the regulating position by the urging force of the spring 74 when no force in pivotally moving direction is imparted on the operation lever 72 because of non-operation to the operation lever 72. The lock lever 70 is movable to the non-regulating position against the urging force of the spring 74 by operating the operation lever 72 of the lock lever 70 which is at the regulating position toward the non-operating position.

In this way, because of the provision of the lock lever 70, free movement of the toner cartridge 152 from the first position to the second position can be restricted, and hence, accidental release of the toner cartridge 152 from the process cartridge 151 can be prevented.

The second side frame 511B of the process cartridge 151 includes a stopper 5115 abuttable on the lock lever 70. The stopper 5115 has a first stop surface 5115*a* abuttable on the locking pawl 71 and a second stop surface 5115*b* abuttable on the pressure lever 73.

The first stop surface 5115*a* prevents the lock lever 70 from further pivotal movement by the abutment of the locking pawl 71 with the first stop surface 5115*a* when the lock lever 70 pivotally moves toward and reaches the regulating position. The second stop surface 5115*b* prevents the lock lever 70 from further pivotal movement by the abutment of the pressure lever 73 with the second stop surface 5115*b* when the lock lever 70 pivotally moves toward and reaches the non-regulating position. Hence, the regulating position and non-regulating position can be determined.

In a state where the process cartridge 151 is attached to the housing 2, the operation lever 72 protrudes rearward of the process cartridge frame 511. For example, the operation lever 72 of the first process cartridge 151-1 protrudes rearward of the cartridge frame 511 of the first process cartridge 151-1, and the operation lever 72 of the first process cartridge 151-1 is positioned between the second process cartridge 151-2 and the cartridge frame 511 of the first process cartridge 151-1.

With this structure, the operation lever 72 of the lock lever 70 is at a narrow position between the first process cartridge 151-1 and the second process cartridge 151-2, and therefore, the operation lever 72 is not easily accessible to the user. Hence, it is difficult for the user to detach only the first toner cartridge 152-1 from the first process cartridge 151-1 attached to the housing 2. Thus, this structure can avoid erroneous detachment operation and can prompt the user to perform correct detachment operation.

Further, in the state where the process cartridge 151 to which the toner cartridge 152 is attached is attached to the housing 2, the position of the operation lever 72 when the lock lever 70 is at the regulating position is lower than the position of the operation lever 72 when the lock lever 70 is at the non-regulating position. That is, in order to operate the lock lever 70 to move from the regulating position to the non-regulating position, the operation lever 72 of the lock lever 70 must be moved upward.

Since the operation lever 72 is at the deep position in the narrow space, it is difficult for the user to operate the operation lever 72 upward to the non-regulating position. Hence, it is difficult for the user to detach only the toner cartridge 152 from the process cartridge 151 attached to the housing 2. Thus, this structure can avoid erroneous detachment operation and can prompt the user to perform correct detachment operation.

Further, the process cartridge 151 according to the second embodiment does not include a handle gripped by the user for detaching the process cartridge 151 from the housing 2. On the other hand, as illustrated in FIG. 19, the toner cartridge 152 includes the toner cartridge handle 521*a* protruding upward. Further, in the state where the process cartridge 151 to which the toner cartridge 152 is attached is attached to the housing 2, the toner cartridge handle 521*a* of the toner cartridge 152 is positioned above the upper end of the process cartridge 151.

With this structure, both the toner cartridge 152 and the process cartridge 151 can be detached from the housing 2 by user's holding and moving the toner cartridge handle 521*a*. At this time, detachment of the process cartridge 151 from the toner cartridge 152 is prevented by the lock lever 70. Since a handle corresponding to the process cartridge handle 518 is not provided, but only the toner cartridge handle 521*a* exists in the process unit 150, the second embodiment leaves the user no other option but to grip the toner cartridge handle 521*a*. Thus, this structure can avoid erroneous detachment operation and can prompt the user to perform correct detachment operation.

Figure 17A:
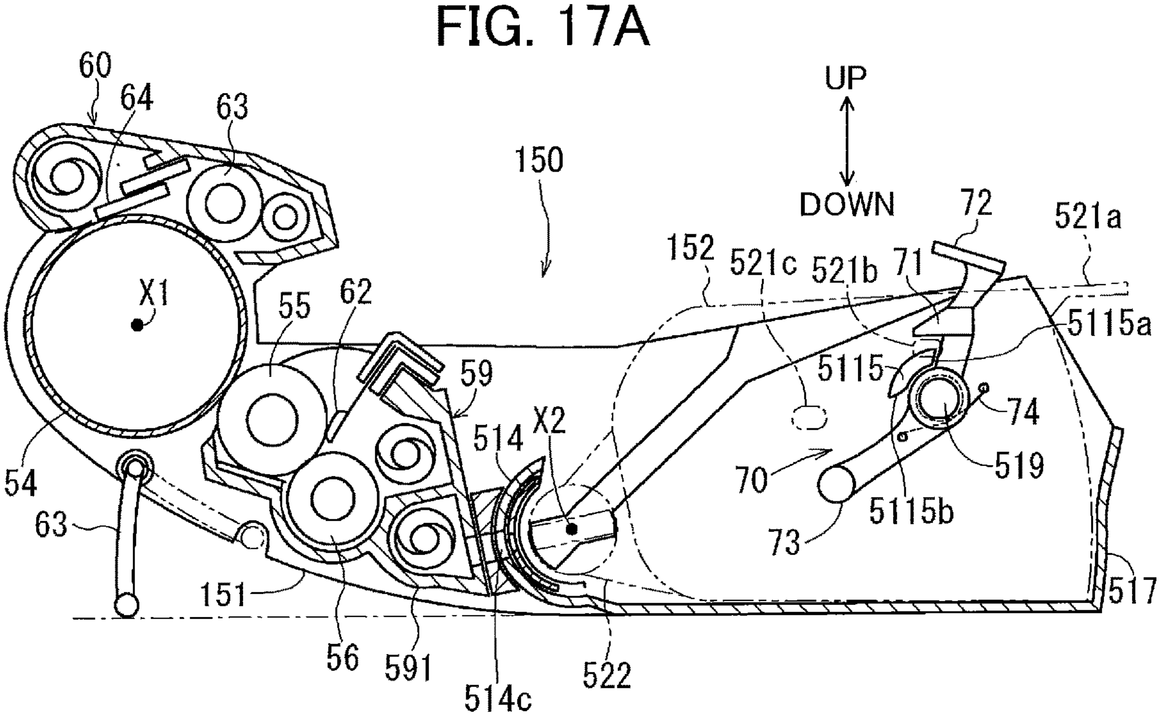
FIG. 17A is a cross-sectional view of the process cartridge having the lock lever and detached from the housing and laid on a horizontal plane to have a horizontal posture, and particularly illustrates a state where the lock lever is at a regulating position and a toner cartridge is at the first position in the image forming apparatus according to the second embodiment.
Figure 17B:
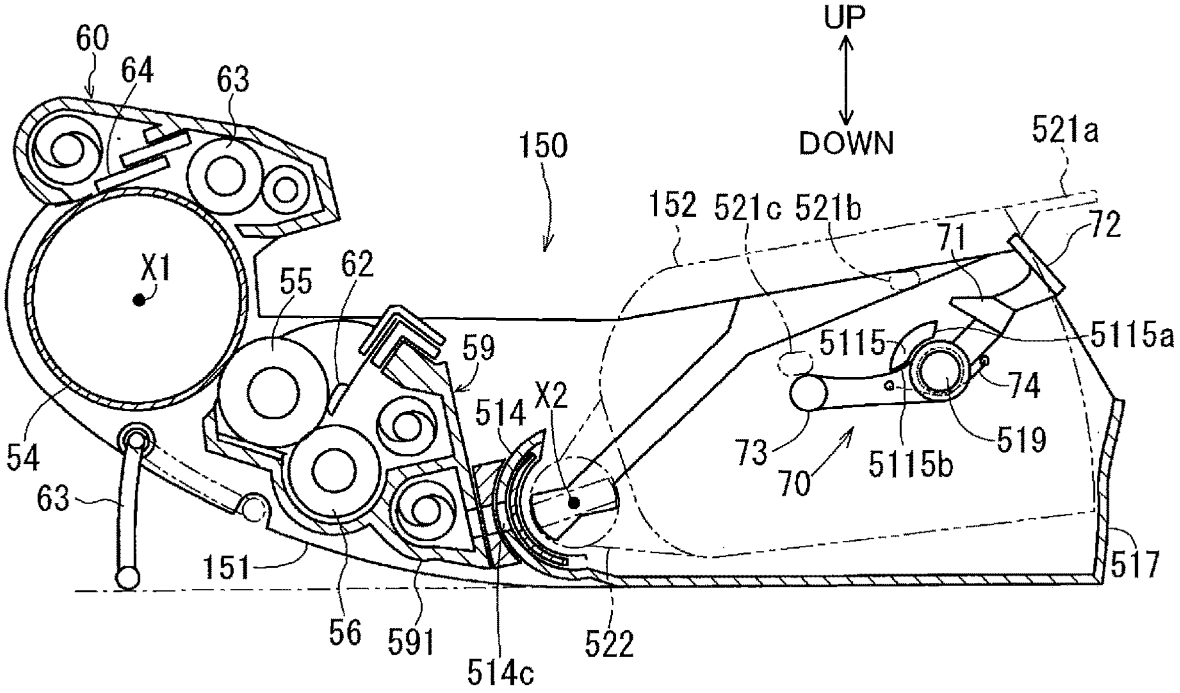
FIG. 17B is a cross-sectional view of the process cartridge having the lock lever and detached from the housing and laid on the horizontal plane to have the horizontal posture, and particularly illustrates a state where the lock lever is at a non-regulating position and the toner cartridge is pushed upward by a pressure lever in the image forming apparatus according to the second embodiment.

Further, as illustrated in FIGS. 17A and 17B, for detaching the toner cartridge 152 from the process cartridge 151 after switching the lock lever 70 from the regulating position to the non-regulating position, the process cartridge 151 to which the toner cartridge 152 is attached is detached from the housing 2, and then the process cartridge 151 is laid on the horizontal plane. Then, the toner cartridge 152 can be removed from the process cartridge 151.

In this case, as illustrated in FIG. 17A, when the user operates the operation lever 72 to move the lock lever 70 from the regulating position to the non-regulating position while the process cartridge 151 is laid on the horizontal plane, the pressure lever 73 is brought into abutment with the second protrusion 521*c* as illustrated in FIG. 17B during the process of movement of the lock lever 70 from the regulating position toward the non-regulating position, so that the second protrusion 521*c* is lifted upward. The toner cartridge 152 is pivotally moved from the first position about the pivot axis X2 in accordance with the lifting movement of the second protrusion 521*c*, and hence the toner cartridge handle 521*a* is moved upward.

Figure 18A:
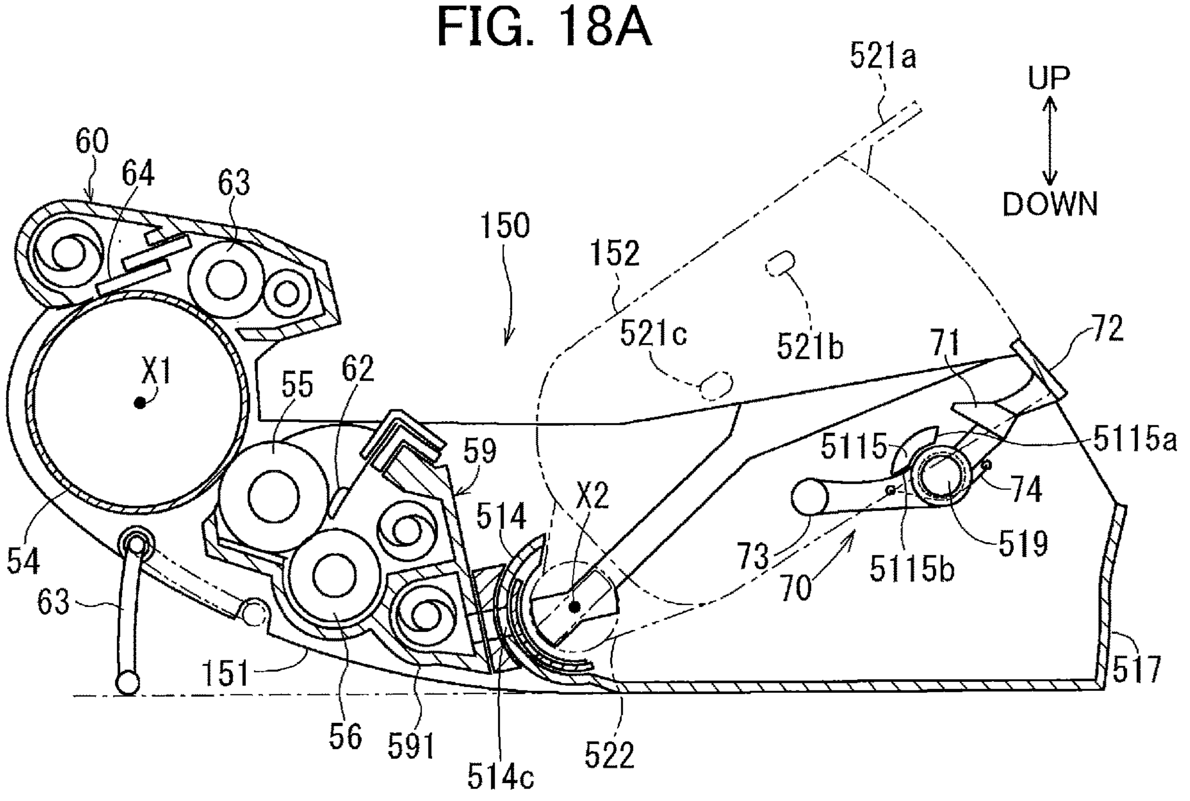
FIG. 18A is a cross-sectional view of the process cartridge having the lock lever and detached from the housing and laid on the horizontal plane to have the horizontal posture, and particularly illustrates a state where the lock lever is at a non-regulating position and the toner cartridge is at the second position in the image forming apparatus according to the second embodiment.

As illustrated in FIG. 18A, the user grips the toner cartridge handle 521*a* moved upward, and further pivotally moves the toner cartridge 152 upward to the second position. Then, the toner cartridge 152 can be detached from the process cartridge 151.

At this time, since the toner cartridge handle 521*a* can be moved upward by switching the lock lever 70 from the regulating position to the non-regulating position, which can facilitate further upward movement of the toner cartridge 152 to the second position by user's gripping and moving the toner cartridge handle 521*a*. Hence, operation for detaching the toner cartridge 152 from the process cartridge 151 can be facilitated.

Figure 18B:
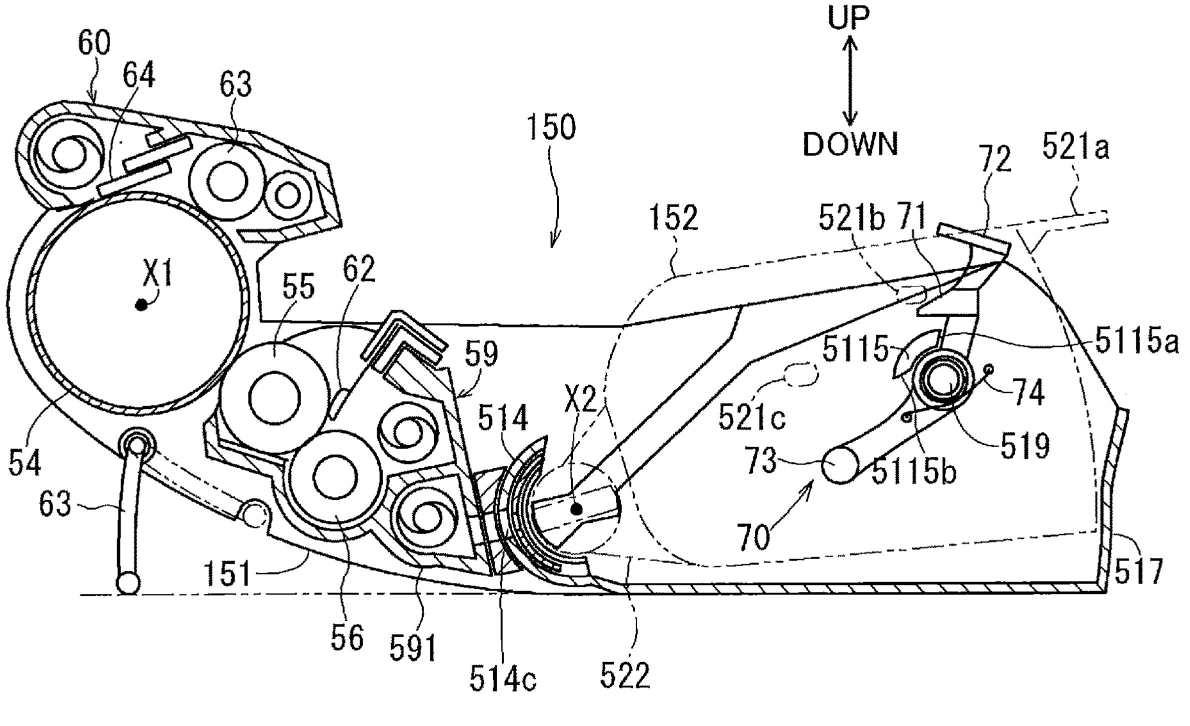
FIG. 18B is a cross-sectional view of the process cartridge having the lock lever and detached from the housing and laid on the horizontal plane to have the horizontal posture, and particularly illustrates a state where a first protrusion of the toner cartridge is brought into abutment with a locking pawl of the lock lever during movement of the toner cartridge from the second position toward the first position in the image forming apparatus according to the second embodiment.

Further, for moving the toner cartridge 152 from the second position to the first position, as illustrated in FIG. 18B, during movement of the toner cartridge 152 from the second position toward the first position, the first protrusion 521*b* of the toner cartridge 152 is brought into abutment with the locking pawl 71 of the lock lever 70, and the first protrusion 521*b* pivotally moves the locking pawl 71 against urging force of the spring 74 such that the lock lever 70 is moved from the regulating position toward the non-regulating position. Hence, the locking pawl 71 is engageable with the first protrusion 521*b* when the toner cartridge 152 is moved to the first position.

Figure 19A:
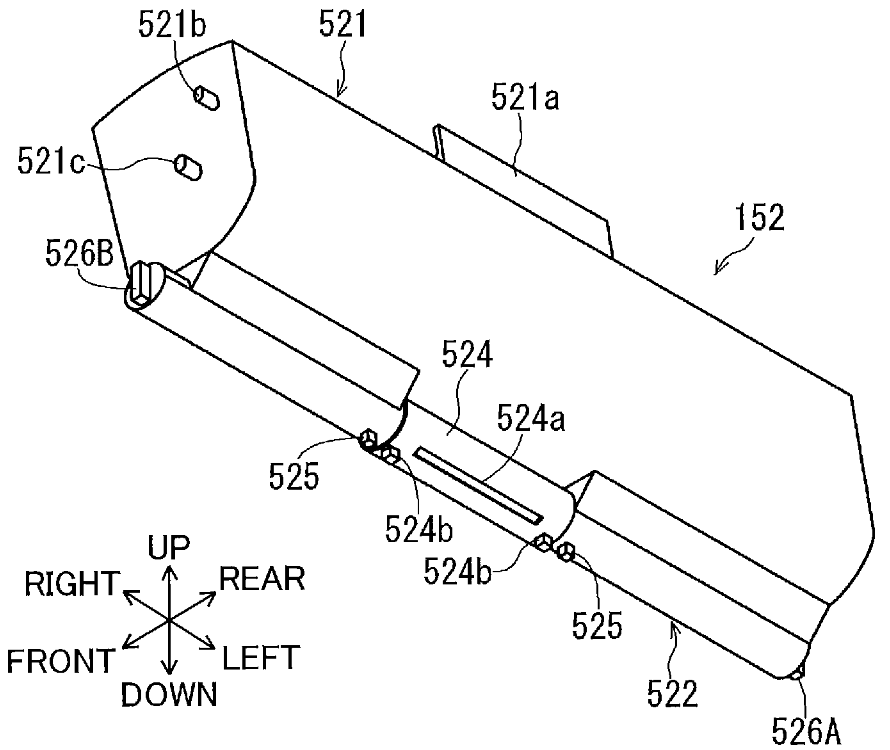
FIG. 19A is a perspective view of the toner cartridge provided with the first protrusion and a second protrusion in the image forming apparatus according to the second embodiment, and particularly illustrates a state where the toner cartridge shutter is closed.
Figure 19B:
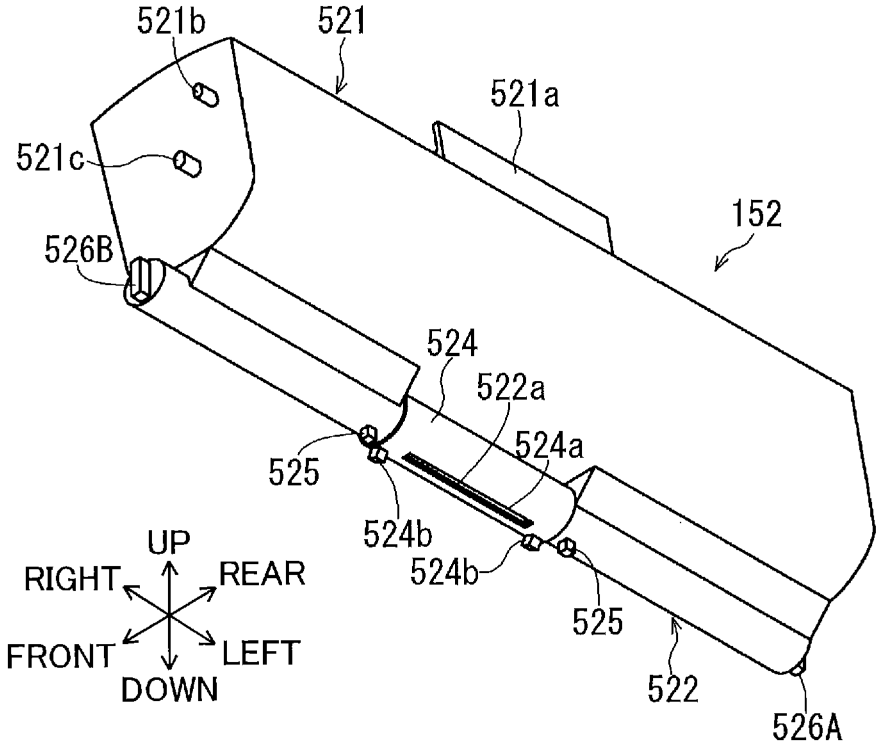
FIG. 19B is a perspective view of the toner cartridge provided with the first protrusion and the second protrusion in the image forming apparatus according to the second embodiment, and particularly illustrates a state where the toner cartridge shutter is open.

In the toner cartridge 52 according to the first embodiment, the toner cartridge shutter 524 is positioned at the left end portion of the connecting portion 522. On the other hand, in the toner cartridge 152 according to the second embodiment, as illustrated in FIGS. 19A and 19B, the toner cartridge shutter 524 is positioned at a center portion in leftward/rightward direction of the connecting portion 522 of the toner cartridge 152. Further, the toner cartridge 152 does not include the waste toner retaining portion 527 that is provided in the toner cartridge 52 of the first embodiment.

Further, as illustrated in FIGS. 20 and 21, the process cartridge shutter 515 of the process cartridge 151 is positioned at a center portion in leftward/rightward direction of the second connection frame 514. Further, the process cartridge 151 does not include the waste toner retaining portion 527 that is provided in the first embodiment.

Figure 23:
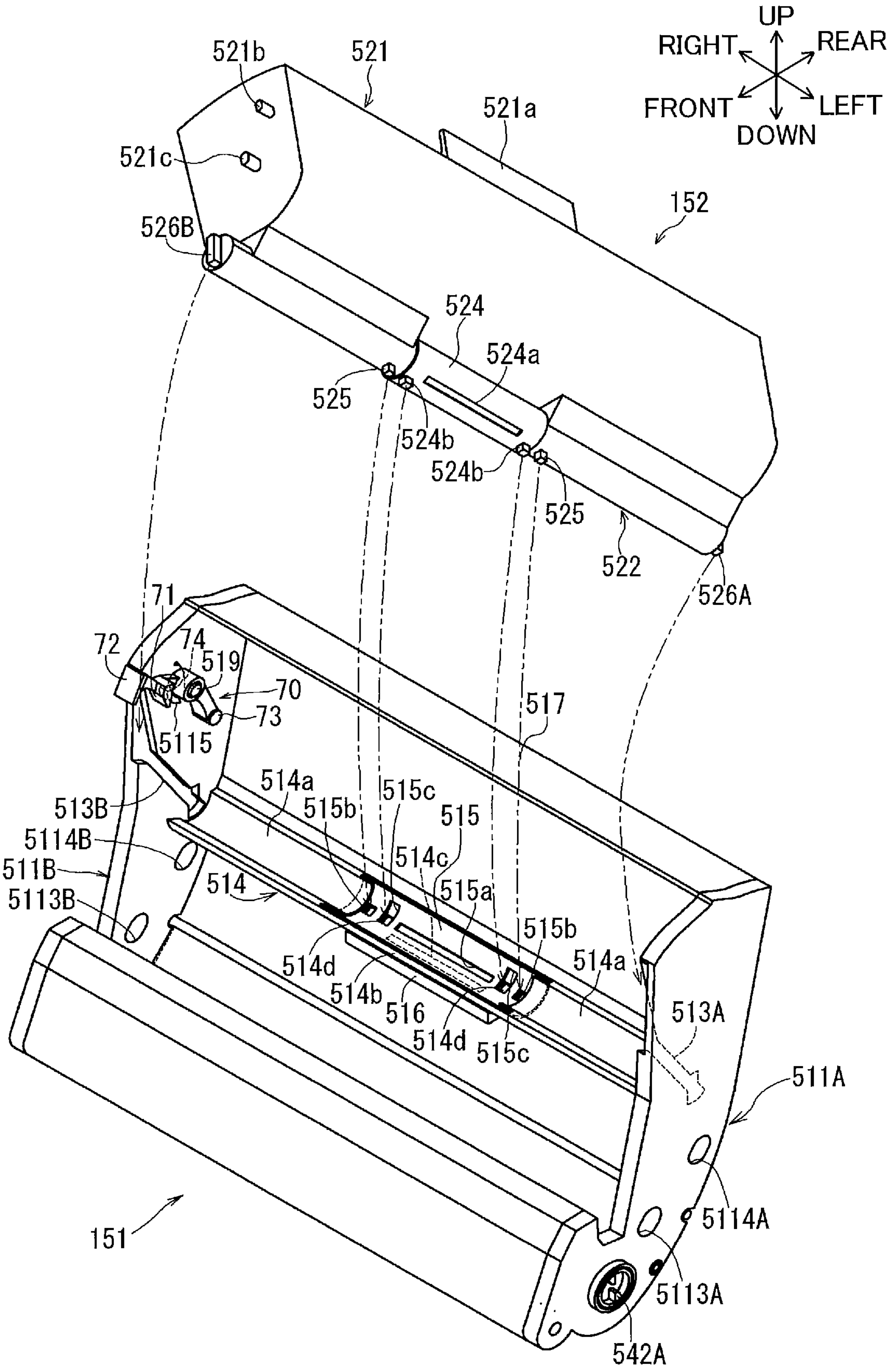
FIG. 23 is a perspective view illustrating a process of attachment of the toner cartridge provided with the first protrusion and the second protrusion to the process cartridge provided with the lock lever, and particularly illustrating engagement of the first protruding portion and the second protruding portion with the first recessed portion and the second recessed portion, respectively.

For attaching the toner cartridge 152 to the process cartridge 151, the guide ribs 526A, 526B of the toner cartridge 152 are inserted into the guide grooves 513A, 513B of the second side frame 511B similar to the first embodiment as illustrated in FIG. 23.

The first protruding portions 524*b* and the second protruding portions 525 of the toner cartridge shutter 524 are engaged with the first recessed portions 514*d* and the second recessed portions 515*b* of the process cartridge 151, respectively.

[Modifications]

According to the image forming apparatus 1, 101 of the first and second embodiments, the top cover 231 can be opened and closed, and the process cartridge 51, 151 is detached from the housing 2 in the open state of the top cover 231.

Figure 24:
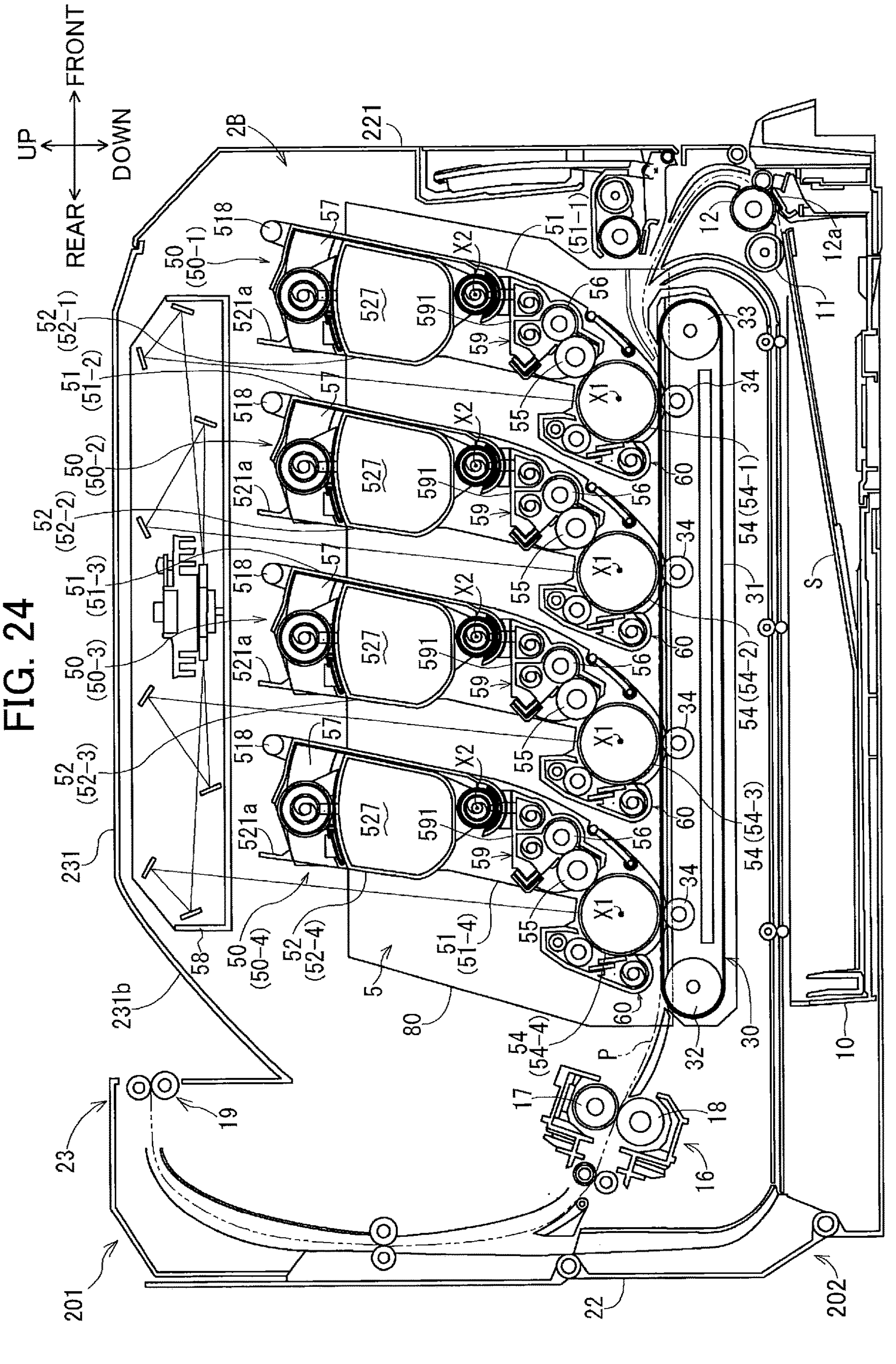
FIG. 24 is a cross-sectional side view illustrating an image forming apparatus according to a first modification where process cartridges are attached to a housing through a drawer, and particularly illustrates the drawer at its internal position.
Figure 25:
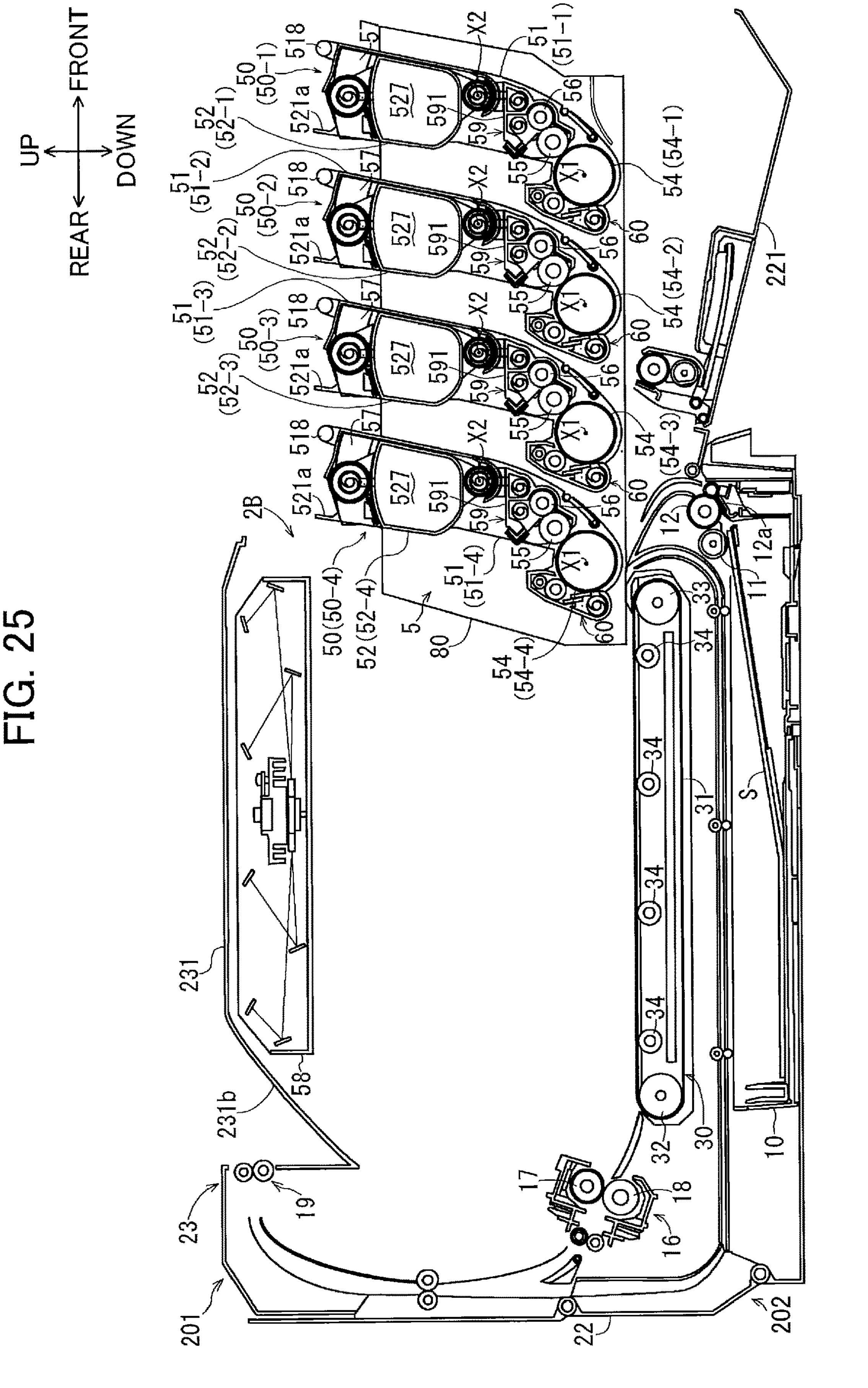
FIG. 25 is a cross-sectional side view illustrating the image forming apparatus according to the first modification, and particularly illustrates the drawer at its external position.

In an image forming apparatus 201 according to a first modification illustrated in FIGS. 24 and 25, the four process cartridges 51 are attachable to and detachable from a housing 202 through a drawer 80. That is, the image forming apparatus 201 includes the drawer 80 movable relative to the housing 202, and four process cartridges 51 are attachable to and detachable from the drawer 80.

The housing 202 has a front opening 2B, and includes a front wall 221 configured to open and close the front opening 2B. Further, the image forming apparatus 201 includes, instead of four exposure heads 53 of the image forming apparatus 1, 101, an exposure unit 58 configured to expose four photosensitive drums 54 to light.

The drawer 80 is movable in frontward/rearward direction between an internal position illustrated in FIG. 24 and an external position illustrated in FIG. 25. When the drawer 80 is at the internal position illustrated in FIG. 24 while the process units 50 (each including the process cartridge 51 and the toner cartridge 52) are attached to the drawer 80, the process units 50 are accommodated in the housing 202.

When the drawer 80 is at the external position illustrated in FIG. 25 while the process units 50 are attached to the drawer 80, at least a part of the process units 50 are exposed to an outside of the housing 202. The process unit(s) 50 exposed to the outside is detachable from the housing 202.

In this way, in the structure where the process cartridge 51 is attached to the housing 202 through the drawer 80, the toner cartridge 52 cannot be detached from the process cartridge 51 in the attached state of the process cartridge 51 to the housing 202, and the toner cartridge 52 can be detached from the process cartridge 51 in the detached state of the process cartridge 51 from the housing 202.

For example, in the image forming apparatus 201, for detaching the first toner cartridge 52-1 from the first process cartridge 51-1 after moving the drawer 80 to the external position, the first toner cartridge 52-1 is mechanically interfered with the first process cartridge 51-1 in the attached state of the first process cartridge 51-1 to the housing 202, preventing the first toner cartridge 52-1 from pivotally moving toward the second position. On the other hand, the first toner cartridge 52-1 can be pivotally moved to the second position to detach the first toner cartridge 52-1 from the first process cartridge 51-1 in the detached state of the first process cartridge 51-1 from the housing 202.

Accordingly, the user has no waver about procedure of detachment of the toner cartridge from the process cartridge avoiding operation mistake. Further, leakage of toner through the toner supply opening 522*a* can be reduced when the toner cartridge 52 is detached from the process cartridge 51.

Figure 26:
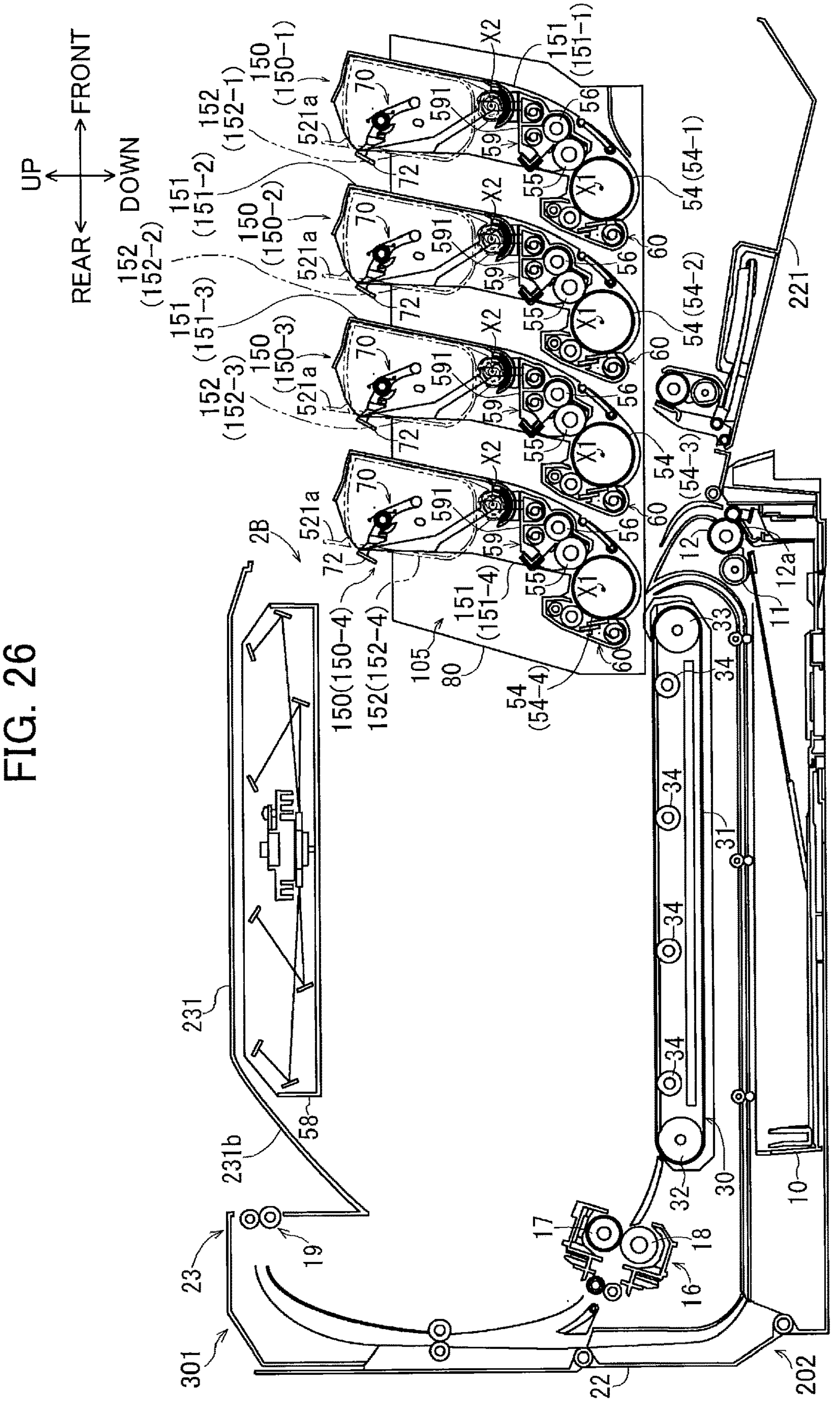
FIG. 26 is a cross-sectional side view illustrating an image forming apparatus according to a second modification where process cartridges each provided with the lock lever are attached to a housing through a drawer.

An image forming apparatus 301 according to a second modification is illustrated in FIG. 26. The image forming apparatus 301 according to the second modification is the same as the image forming apparatus 201 according to the first modification except that the process cartridge 151 and the toner cartridge 152 are employed instead of the process cartridge 51 and the toner cartridge 52.

In the image forming apparatus 301, in the attached state of the process cartridge 151 to the housing 202, the operation lever 72 of the first process cartridge 151-1 is at a position between the body of the first process cartridge 151-1 and the second process cartridge 151-2. Hence, the operation lever 72 of the first process cartridge 151-1 is not accessible to the user. Further, upward pivotal movement is required for pivotally moving the lock lever 70 from the regulating position toward the non-regulating position. However, such an upward movement cannot be carried out because of difficult accessibility to the operation lever 72.

While the description has been made in detail with reference to the specific embodiments and modifications, it would be apparent to those skilled in the art that various changes and modifications may be made therein.

What is claimed is:

1. An image forming apparatus comprising:

a housing;

a first process cartridge attachable to and detachable from the housing, the first process cartridge comprising:

a first photosensitive drum having one end portion and another end portion in a direction of a rotation axis;

a first developing roller; and a developing frame supporting the first developing roller and having a toner inlet opening;

a toner cartridge having a toner supply opening, the toner cartridge being positioned above the developing frame such that the toner supply opening and the toner inlet opening face with each other in upward/downward direction perpendicular to the direction of the rotation axis, the toner cartridge being pivotally movable between a first position and a second position relative to the first process cartridge about a pivot axis extending parallel to the direction of the rotation axis of the first photosensitive drum in a state where the toner cartridge is supported by the first process cartridge, the toner cartridge being incapable of being detached from the first process cartridge in the first position, and the toner cartridge being detachable from the first process cartridge in the second position; and a second process cartridge attachable to and detachable from the housing and juxtaposed to the first process cartridge, the second process cartridge positioned adjacent to the first process cartridge in a direction of movement of the toner cartridge from the first position to the second position, wherein the first process cartridge further comprises:

a first side frame rotatably supporting the one end portion of the first photosensitive drum and extending in upward/downward direction perpendicular to the direction of the rotation axis;

a second side frame rotatably supporting the another end portion of the first photosensitive drum and extending in upward/downward direction perpendicular to the direction of the rotation axis; and a first guide and a second guide which are provided in inner side surfaces of the first side frame and the second side frame, respectively, in the direction of the rotation axis, and configured to guide the toner cartridge when the toner cartridge is attached to the first process cartridge, each of the first guide and the second guide extending in a direction inclined relative to upward/downward direction, wherein each of the first guide and the second guide is inclined such that an upper open end of each of the first guide and the second guide opens to face the second process cartridge in a state where the first process cartridge is attached to the housing and the second process cartridge is attached to the housing, thereby preventing the toner cartridge from being detached from the first process cartridge.

2. The image forming apparatus according to claim 1, wherein in a state where the toner cartridge is attached to the first process cartridge, the pivot axis of the toner cartridge is positioned at a lower end of each of the first guide and the second guide, the first guide and the second guide being inclined relative to upward/downward direction such that the upper open ends of the first guide and the second guide are closer to the second process cartridge than the lower ends of the first guide and the second guide are to the second process cartridge.

3. The image forming apparatus according to claim 2, wherein in the state where the first process cartridge is attached to the housing and the second process cartridge is attached to the housing, an extension line of the first guide and an extension line of the second guide intersect the second process cartridge, the extension line of the first guide extending from the upper open end of the first guide in a direction that is defined from the lower end of the first guide to the upper open end of the first guide, the extension line of the second guide extending from the upper open end of the second guide in a direction that is defined from the lower end of the second guide to the upper open end of the second guide.

4. The image forming apparatus according to claim 1, wherein in the state where the first process cartridge is attached to the housing and the second process cartridge are attached to the housing, the toner cartridge attached to the first process cartridge is abuttable against the second process cartridge as a result of movement of the toner cartridge from the first position toward the second position, thereby preventing further movement of the toner cartridge toward the second position to prevent the toner cartridge from being detached from the first process cartridge.

5. The image forming apparatus according to claim 1, wherein the toner cartridge further comprises a toner cartridge shutter movable between a closed position, where the toner cartridge shutter closes the toner supply opening, and an open position, where the toner cartridge shutter opens the toner supply opening, wherein the first process cartridge further comprises a process cartridge shutter movable between a closed position, where the process cartridge shutter closes the toner inlet opening, and an open position, where the process cartridge shutter opens the toner inlet opening, wherein when the toner cartridge is at the first position, the toner cartridge shutter is at the open position opening the toner supply opening and the process cartridge shutter is at the open position opening the toner inlet opening, and wherein when the toner cartridge is at the second position, the toner cartridge shutter is at the closed position closing the toner supply opening and the process cartridge shutter is at the closed position closing the toner inlet opening.

6. The image forming apparatus according to claim 1, wherein the first process cartridge further comprises a first connection frame connecting an upper end portion of the first side frame to an upper end portion of the second side frame, the first connecting frame constituting an upper end portion of the first process cartridge when the first process cartridge is attached to the housing, and wherein when the first process cartridge is attached to the housing and the toner cartridge is attached to the first process cartridge, the first connection frame is positioned opposite to the first photosensitive drum with respect to the toner cartridge in upward/downward direction.

7. The image forming apparatus according to claim 6, wherein the toner cartridge faces the first connection frame when the toner cartridge is at the first position, and the toner cartridge is offset from the first connection frame when the toner cartridge is at the second position.

8. The image forming apparatus according to claim 6, wherein the developing frame is movably supported by the first side frame and the second side frame, wherein the first process cartridge further comprises a second connection frame having one end connected to the first side frame and another end connected to the second side frame, the toner inlet opening being formed in the second connection frame, and a seal member, wherein the developing frame is formed with an opening in communication with an interior of the developing frame and facing the toner inlet opening, and wherein the seal member is positioned between the second connection frame and the developing frame to seal a peripheral edge portion of the toner inlet opening and a peripheral edge portion of the opening.

9. The image forming apparatus according to claim 1, further comprising a sheet supply tray positioned at a lower internal portion of the housing, wherein the second process cartridge comprises a second photosensitive drum and a second developing roller, wherein the housing comprises one end wall and another end wall opposite to the one end wall in a first direction which is perpendicular to the direction of the rotation axis of the first photosensitive drum, wherein the second process cartridge is attachable to the housing in a juxtaposed relation in the first direction with respect to the first process cartridge attached to the housing, wherein a rotation axis of the second photosensitive drum extends parallel to the rotation axis of the first photosensitive drum, wherein the sheet supply tray is configured to be pulled out of the housing in the first direction and in the direction from the one end wall to the another end wall, wherein the first process cartridge further comprises a process cartridge handle, wherein the toner cartridge further comprises a toner cartridge handle, and wherein in a state where the first process cartridge is attached to the housing, the process cartridge handle is positioned closer to the another end wall than the toner cartridge handle is to the another end wall.

10. The image forming apparatus according to claim 1, wherein the first process cartridge further comprises a regulation member movable between a regulating position where the regulation member prevents the toner cartridge from moving from the first position to the second position and a non-regulating position where the regulation member permits the toner cartridge to move from the first position to the second position, and wherein the regulation member comprises an operation lever configured to perform switching operation between the regulating position and the non-regulating position.

11. The image forming apparatus according to claim 10, wherein the second process cartridge is positioned in a juxtaposed relation with respect to the first process cartridge attached to the housing in a direction perpendicular to the direction of the rotation axis of the first photosensitive drum, wherein the operation lever is positioned between the first process cartridge attached to the housing and the second process cartridge attached to the housing.

12. The image forming apparatus according to claim 10, wherein when the first process cartridge, to which the toner cartridge is attached, is attached to the housing, the operation lever at the regulating position of the regulation member is positioned lower than the operation lever at the non-regulating position of the regulation member.

13. The image forming apparatus according to claim 10, wherein the toner cartridge further comprises a toner cartridge handle protruding upward and positioned above an upper end of the first process cartridge in the state where the first process cartridge to which the toner cartridge is attached is attached to the housing.

14. The image forming apparatus according to claim 10, wherein the toner cartridge comprises a toner cartridge casing in which toner is accommodatable.

15. The image forming apparatus according to claim 14, wherein the toner cartridge further comprises a first protrusion protruding from the toner cartridge casing, and wherein the regulation member is engaged with the first protrusion when the regulation member is at the regulating position preventing the toner cartridge from moving from the first position to the second position.

16. The image forming apparatus according to claim 14, wherein the toner cartridge further comprises a second protrusion protruding from the toner cartridge casing, and wherein the regulation member is abuttable on the second protrusion during movement of the regulation member from the regulating position toward the non-regulating position to move the toner cartridge toward the second position.

17. The image forming apparatus according to claim 10, wherein the regulation member is pivotally movably supported by the second side frame, and wherein the second side frame is provided with a stopper abuttable on the regulation member, the stopper having a first stop surface to stop the regulation member at the regulating position and a second stop surface to stop the regulation member at the non-regulating position.

18. The image forming apparatus according to claim 1, wherein the developing frame accommodates therein toner, and wherein the toner inlet opening is configured to communicate with an interior of the developing frame.

19. The image forming apparatus according to claim 1, wherein the toner cartridge is attachable to and detachable from the first process cartridge, wherein the toner cartridge comprises a toner cartridge casing in which toner is accommodatable, the toner cartridge casing being formed with the toner supply opening, and wherein the toner is configured to be passed through the toner supply opening.

20. The image forming apparatus according to claim 1, wherein in the state where the toner cartridge is attached to the first process cartridge and the first process cartridge is attached to the housing, the toner cartridge is positioned above the developing frame such that the toner supply opening and the toner inlet opening face with each other in upward/downward direction.

21. The image forming apparatus according to claim 1, wherein the housing has an opening and comprises a cover configured to open and close the opening, and wherein, when the opening is opened by the cover, the first process cartridge is exposed to an outside of the housing through the opening.

22. The image forming apparatus according to claim 1, further comprising a drawer movable relative to the housing between an internal position and an external position, the drawer being accommodated inside the housing in the internal position, at least a part of the drawer being exposed to the outside of the housing in the external position, the first process cartridge and the second process cartridge being attachable to and detachable from the drawer, wherein, when the drawer is positioned in the external position, the first process cartridge is exposed to the outside of the housing.

* * * * *